(12) United States Patent
Kleemann et al.

(10) Patent No.: US 7,078,414 B2
(45) Date of Patent: Jul. 18, 2006

(54) DERIVATIVES OF 3-GUANIDINOCARBONYL-1-HETEROARYL-PYRROLE, PREPARATION PROCESS AND INTERMEDIATES OF THIS PROCESS, THEIR USE AS MEDICAMENTS, AND PHARMACEUTICAL COMPOSITIONS COMPRISING THEM

(75) Inventors: Heinz-Werner Kleemann, Bischofsheim (DE); Pascal Desmazeau, Tigery (FR); Jean-Christophe Carry, Saint Maur des Fosses (FR); Baptiste Ronan, Clamart (FR); Serge Mignani, Chatenay-Malabry (FR); Jean Bououerel, Drancy (FR); Arielle Genevois-Borella, Thiais (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 35 days.

(21) Appl. No.: 10/745,909

(22) Filed: Dec. 23, 2003

(65) Prior Publication Data

US 2004/0266775 A1   Dec. 30, 2004

Related U.S. Application Data

(63) Continuation of application No. PCT/EP03/07021, filed on Jul. 2, 2003.

(30) Foreign Application Priority Data

Jul. 16, 2002   (FR) .................................. 02 08947

(51) Int. Cl.
*A61K 31/47* (2006.01)
*A61K 31/40* (2006.01)
*C07D 215/02* (2006.01)
*C07D 301/27* (2006.01)

(52) U.S. Cl. ..................... 514/314; 514/422; 514/426; 546/167; 549/517; 549/518

(58) Field of Classification Search ................ 549/517, 549/518; 546/167; 514/314, 422, 426
See application file for complete search history.

(56) References Cited

U.S. PATENT DOCUMENTS 5,698,581 A   12/1997 Kleemann

FOREIGN PATENT DOCUMENTS

WO   WO 94/26709   11/1994
WO   WO 99/43663   9/1999

OTHER PUBLICATIONS

Guzman_Perez et al, Discovery of Zoniporide: A Potent and Selective Sodium-Hydrogen Exchanger Type 1 (NHE-1) Inhibitor with High Aqueous Solubility, Bioorganic & Medicinal Chemistry Letters vol. 11; No. 6: (2001); pp. 803-807.

*Primary Examiner*—D. Margaret Seaman
(74) *Attorney, Agent, or Firm*—Joseph D. Rossi

(57) ABSTRACT

The present invention relates to 3-guanidinocarbonyl-1-heteroaryl-pyrrole derivatives of formula (I) wherein $R_1$ to $R_3$ and Ar are as defined herein, pharmaceutical compositions comprising such derivatives, methods of treatment comprising administering such derivatives, and processes for their preparation

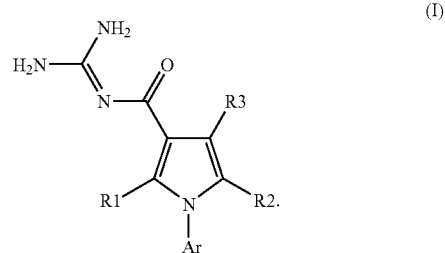

25 Claims, No Drawings

DERIVATIVES OF 3-GUANIDINOCARBONYL-1-HETEROARYL-PYRROLE, PREPARATION PROCESS AND INTERMEDIATES OF THIS PROCESS, THEIR USE AS MEDICAMENTS, AND PHARMACEUTICAL COMPOSITIONS COMPRISING THEM

FIELD OF THE INVENTION

The present invention relates to 3-guanidinocarbonyl-1-heteroaryl-pyrrole derivatives of formula (I)

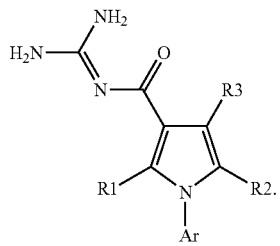

or pharmaceutically acceptable salts thereof and their use as NHE inhibitors, especially NHE1 inhibitors. The inventive compounds are suitable for example as antiarrhythmic medicaments with a cardioprotective component for infarction prophylaxis and infarction treatment and for the treatment of angina pectoris. They also inhibit in a preventive manner the pathophysiological processes associated with the development of ischemia-induced damage, in particular in the triggering of ischemia-induced cardiac arrhythmias and of heart failure.

BACKGROUND OF THE INVENTION

Patent EP0676395 discloses heteroaroylguanidine derivatives as NHE inhibitors, including generically 3-guanidinocarbonyl-1-heteroaryl-pyrrole derivatives of formula (I). The inventive compounds of formula I show a suprisingly high activity as NHE1 inhibitors together with a good selectivity between NHE1 and NHE2.

The compounds of formula (I) can be used as novel medicaments in the treatment of diseases as inhibitors of NHE and in particular of NHE-1 with good selectivity for NHE-1 with respect to NHE-2. This good selectivity makes it possible to reduce the potential gastrointestinal side effects existing with regard to molecules having inadequate selectivity (J. Clin. Invest., 1998, 101(6), 1243; Comparative Medicine, 2000, 50(5), 511).

Since NHE inhibitors predominantly act via their effect on cellular pH regulation, they can generally be combined beneficially with other compounds which regulate the intracellular pH, with suitable combination partners being for example inhibitors of the carbonate dehydratase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

SUMMARY OF THE INVENTION

The invention relates to a compound of formula 1,

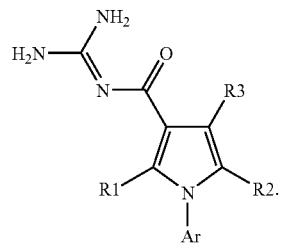

wherein
$R_1$ is hydrogen or methyl,
$R_2$ is hydrogen or $C_1$–$C_6$ alkyl,
$R_3$ is hydrogen, $C_1$–$C_6$ alkyl, $C_3$–$C_6$ cycloalkyl, halogen, $C_1$–$C_6$ hydroxyalkyl, $C_1$–$C_6$ alkyl-$NR_aR_b$, $NR_aR_b$, $S(O)_n R_4$ or $C_1$–$C_6$ polyfluoroalkyl,
n is 0, 1 or 2,
Ar is a 6-membered monocyclic or a 10-membered bicyclic heteroaryl having one or two nitrogen atoms, which may be linked via any of its positions and which is optionally substituted on all their other positions with $C_1$–$C_6$ alkyl, halogen, nitro, $NR_aR_b$, $C_1$–$C_4$ alkylcarbonylamino, hydroxy, $C_1$–$C_6$ alkoxy, $S(O)_n R_4$, $CO_2H$, $C_1$–$C_6$ alkoxycarbonyl, $C_1$–$C_6$ alkylcarbonyl, $CONR_aR_b$, CN, $C_1$–$C_4$ polyfluoroalkyl, $C_1$–$C_3$ polyfluoroalkoxy or $SO_3H$,
$R_a$ and $R_b$ are each, independently, hydrogen, linear or branched $C_1$–$C_6$ alkyl, or $R_a$ and $R_b$ form, together with the nitrogen atom to which they are attached, a 5- or 6-membered heterocycle, which optionally contain another heteroatom chosen from O, S and N,
and
$R_4$ is $C_1$–$C_6$ alkyl, $C_1$–$C_6$ alkylamino or $NH_2$, or a racemic mixture, enantiomer, diastereomer, or tautomer of such compound, or a mixture thereof, or a pharmaceutically acceptable salt of such compound, racemic mixture, enantiomer, diastereomer, tautomer, or mixture.

DETAILED DESCRIPTION OF THE INVENTION

Definition of Terms
As used above, and throughout the description of the invention, the following terms, unless otherwise indicated, shall be understood to have the following meanings.

$NR_aR_b$ in the definitions of $R_3$ and Ar of formula I are chosen independently of each other.

$R_4$ in the definitions of $R_3$ and Ar of formula I are chosen independently of each other.

Alkyl is straight or branched. Example of alkyl is methyl, ethyl, n-propyl, isopropyl (=1-methylethyl), n-butyl, isobutyl (=2-methylpropyl), sec-butyl (=1-methylpropyl), tert-butyl (=1,1-dimethylethyl), pentyl or hexyl. Preferred alkyl is methyl, ethyl, n-propyl, isopropyl, tert-butyl or isobutyl.

One or more, for example, 1, 2, 3, 4, 5, 6, 7, 8, or 9 hydrogen atoms in alkyl may be replaced by fluorine atoms to form polufluoroalkyl. Example of polyfluoroalkyl is difluoromethyl, trifluoromethyl, pentafluoroethyl, 2,2,2-trifluoroethyl or 3,3,3-trifluoropropyl.

Polyfluoroalkoxy is a $C_1$–$C_3$ alkoxy substituted by 1, 2, 3, 4, 5, 6 or 7 fluorine atoms, in particular trifluoromethoxy.

Example of cycloalkyl is cyclopropyl, cyclobutyl, cyclopentyl or cyclohexyl. Cycloalkyl is optionally substituted by fluorine, chlorine, bromine or iodine, in particular by fluorine.

Heterocycle is saturated or unsaturated. Example of heterocycle is piperidin-1-yl, pyrrolidin-1-yl, morpholin-4-yl, thiomorpholin-4-yl or piperazin-1-yl.

Example of heteroaryl is pyridyl, pyrimidine, chinoline, pyridazine, pyrazine, quinazoline, quinoxaline, phthalazine, isochinoline or cinnoline, preferably pyridyl, pyrimidine, chinoline, isochinoline or cinnoline.

Halogen is chlorine, bromine, fluorine or iodine.

Patient includes both human and other mammals.

Pharmaceutically effective amount means an amount of the compound according to the invention effective in producing the desired therapeutic effect.

Particular or Preferred Embodiment

A preferred embodiment of the compound of formula I is wherein
$R_1$ is hydrogen or methyl,
$R_2$ is hydrogen or $C_1$–$C_6$ alkyl,
$R_3$ is hydrogen, $C_1$–$C_6$ alkyl, $C_3$–$C_6$ cycloalkyl, halogen, $C_1$–$C_6$ hydroxyalkyl, $C_1$–$C_6$ alkyl-$NR_aR_b$, $NR_aR_b$, $S(O)_n R_4$ or $C_1$–$C_6$ polyfluoroalkyl,
n is 0, 1 or 2,
Ar is quinoline, isoquinoline, pyridine, pyrimidine or cinnoline, which may be linked via any of its positions and which is optionally substituted on all their other positions with $C_1$–$C_6$ alkyl, halogen, nitro, $NR_aR_b$, $C_1$–$C_4$ alkylcarbonylamino, hydroxy, $C_1$–$C_6$ alkoxy, $S(O)_n R_4$, $CO_2H$, $C_1$–$C_6$ alkoxycarbonyl, $C_1$–$C_6$ alkylcarbonyl, $CONR_aR_b$, CN, $C_1$–$C_4$ polyfluoroalkyl, $C_1$–$C_3$ polyfluoroalkoxy or $SO_3H$,
$R_a$ and $R_b$ are each, independently, hydrogen, linear or branched $C_1$–$C_6$ alkyl having or $R_a$ and $R_b$ form, together with the nitrogen atom to which they are attached, a 5- or 6-membered heterocycle, which optionally contain another hetero atom chosen from O, S and N, and
$R_4$ is $C_1$–$C_6$ alkyl, $C_1$–$C_6$ alkylamino or $NH_2$.

A further preferred embodiment of the compound of formula I is wherein
$R_1$ is hydrogen or methyl,
$R_2$ is hydrogen or $C_1$–$C_6$ alkyl,
$R_3$ is hydrogen, methyl, cyclopropyl or $CF_3$,
Ar is quinoline, isoquinoline, pyridine, pyrimidine or cinnoline, which may be linked via any of its positions and which is optionally substituted on all their other positions with $C_1$–$C_6$ alkyl, halogen, nitro, $NR_aR_b$, $C_1$–$C_4$ alkylcarbonylamino, hydroxy, $C_1$–$C_6$ alkoxy, $S(O)_n R_4$, $CO_2H$, $C_1$–$C_6$ alkoxycarbonyl, $C_1$–$C_6$ alkylcarbonyl, $CONR_aR_b$, CN, $C_1$–$C_4$ polyfluoroalkyl, $C_1$–$C_3$ polyfluoroalkoxy or $SO_3H$,
n is 0, 1 or 2,
$R_a$ and $R_b$ are each, independently, hydrogen, linear or branched $C_1$–$C_6$ alkyl or $R_a$ and $R_b$ form, together with the nitrogen atom to which they are attached, a 5- or 6-membered heterocycle, which optionally contain another hetero atom chosen from O, S and N,
and
$R_4$ is $C_1$–$C_6$ alkyl, $C_1$–$C_6$ alkylamino or $NH_2$.

A preferred embodiment of the compound of formula I is wherein $R_1$ is hydrogen or methyl.

A preferred embodiment of the compound of formula I is wherein $R_2$ is hydrogen or methyl.

A particularly preferred embodiment of the compound of formula I is wherein $R_2$ is hydrogen.

A preferred embodiment of the compound of formula I is wherein $R_3$ is hydrogen, $C_1$–$C_6$ alkyl, cyclopropyl, isopropyl, dimethylamino or $CF_3$.

A particularly preferred embodiment of the compound of formula I is wherein $R_3$ is hydrogen, methyl, cyclopropyl or $CF_3$.

A preferred embodiment of the compound of formula I is wherein Ar is optionally substituted once or twice by methyl, ethyl, F, Cl, Br, hydroxy, methoxy, ethoxy or $CF_3$.

A particularly preferred embodiment of the compound of formula I is wherein Ar is optionally substituted once or twice by methyl, F, Cl, methoxy or $CF_3$.

Very particularly preferred species according to the invention is that of formula 1, which is:
3-guanidinocarbonyl-1-(quinol-2-yl)-1H-pyrrole,
3-guanidinocarbonyl-1-(quinol-4-yl)-1H-pyrrole,
3-guanidinocarbonyl-2-methyl-1-(quinol-4-yl)-1H-pyrrole,
3-guanidinocarbonyl-2-methyl-1-(quinol-2-yl)-1H-pyrrole,
3-guanidinocarbonyl-1-(isoquinol-1-yl)-1H-pyrrole,
3-guanidinocarbonyl-1-(isoquinol-1-yl)-2-methyl-1H-pyrrole,
3-guanidinocarbonyl-1-(quinol-5-yl)-1H-pyrrole,
3-guanidinocarbonyl-1-(quinol-8-yl)-1H-pyrrole,
3-guanidinocarbonyl-1-(isoquinol-4-yl)-1H-pyrrole,
3-guanidinocarbonyl-4-methyl-1-(quinol-4-yl)-1H-pyrrole,
3-guanidinocarbonyl-1-(isoquinol-1-yl)-4-methyl-1H-pyrrole,
3-guanidinocarbonyl-4,5-dimethyl-1-(quinol-4-yl)-1H-pyrrole,
3-guanidinocarbonyl-4-methyl-1-(quinol-5-yl)-1H-pyrrole,
3-guanidinocarbonyl-4-methyl-1-(quinol-2-yl)-1H-pyrrole,
3-guanidinocarbonyl-4-cyclopropyl-1-(quinol-4-yl)-1H-pyrrole,
3-guanidinocarbonyl-4-isopropyl-1-(quinol-4-yl)-1H-pyrrole,
3-guanidinocarbonyl-4-trifluoromethyl-1-(quinol-4-yl)-1H-pyrrole,
3-guanidinocarbonyl-4-dimethylamino-1-(quinol-4-yl)-1H-pyrrole,
3-guanidinocarbonyl-4-chloro-1-(quinol-4-yl)-1H-pyrrole,
3-guanidinocarbonyl-1-(2-methylquinol-4-yl)-1H-pyrrole,
3-guanidinocarbonyl-4-methyl-1-(2-methylquinol-4-yl)-1H-pyrrole,
3-guanidinocarbonyl-1-(6-chloroquinol-4-yl)-1H-pyrrole,
3-guanidinocarbonyl-4-methyl-1-(6-chloroquinol-4-yl)-1H-pyrrole,
3-guanidinocarbonyl-1-(7-chloroquinol-4-yl)-1H-pyrrole,
3-guanidinocarbonyl-4-methyl-1-(7-chloroquinol-4-yl)-1H-pyrrole,
3-guanidinocarbonyl-1-(8-chloroquinol-4-yl)-1H-pyrrole,
3-guanidinocarbonyl-4-methyl-1-(8-chloroquinol-4-yl)-1H-pyrrole,
3-guanidinocarbonyl-1-(7-chloro-2-methylquinol-4-yl)-1H-pyrrole,
3-guanidinocarbonyl-4-methyl-1-(7-chloro-2-methylquinol-4-yl)-1H-pyrrole,
3-guanidinocarbonyl-1-(6-fluoroquinol-4-yl)-1H-pyrrole,
3-guanidinocarbonyl-4-methyl-1-(6-fluoroquinol-4-yl)-1H-pyrrole,
3-guanidinocarbonyl-1-(8-fluoroquinol-4-yl)-1H-pyrrole,
3-guanidinocarbonyl-4-methyl-1-(8-fluoroquinol-4-yl)-1H-pyrrole,
3-guanidinocarbonyl-1-(6-fluoro-2-methylquinol-4-yl)-1H-pyrrole,
3-guanidinocarbonyl-4-methyl-1-(6-fluoro-2-methylquinol-4-yl)-1H-pyrrole, 3-guanidinocarbonyl-1-(7-fluoro-2-methylquinol-4-yl)-1H-pyrrole,
3-guanidinocarbonyl-4-methyl-1-(7-fluoro-2-methylquinol-4-yl)-1H-pyrrole,
3-guanidinocarbonyl-1-(8-fluoro-2-methylquinol-4-yl)-1H-pyrrole,
3-guanidinocarbonyl-4-methyl-1-(8-fluoro-2-methylquinol-4-yl)-1H-pyrrole,
3-guanidinocarbonyl-1-(6,8-difluoroquinol-4-yl)-1H-pyrrole,
3-guanidinocarbonyl-4-methyl-1-(6,8-difluoroquinol-4-yl)-1H-pyrrole,
3-guanidinocarbonyl-4-methyl-1-(6-methoxyquinol-4-yl)-1H-pyrrole,
3-guanidinocarbonyl-4-methyl-1-(6-hydroxyquinol-4-yl)-1H-pyrrole,
3-guanidinocarbonyl-4-methyl-1-(7-methoxyquinol-4-yl)-1H-pyrrole,
3-guanidinocarbonyl-4-methyl-1-(7-hydroxyquinol-4-yl)-1H-pyrrole,
3-guanidinocarbonyl-4-methyl-1-(6-trifluoromethylquinol-4-yl)-1H-pyrrole,
3-guanidinocarbonyl-4-methyl-1-(7-trifluoromethylquinol-4-yl)-1H-pyrrole,
3-guanidinocarbonyl-1-(isoquinol-1-yl)-4-trifluormethyl-1H-pyrrole,
3-guanidinocarbonyl-1-(1-cinnolin-4-yl)-1H-pyrrole,
3-guanidinocarbonyl-4-methyl-1-(pyrimidin-2-yl)-1H-pyrrole,
3-guanidinocarbonyl-4-methyl-1-(pyridin-2-yl)-1H-pyrrole,
3-guanidinocarbonyl-4-methyl-1-(pyridin-3-yl)-1H-pyrrole,
3-guanidinocarbonyl-4-methyl-1-(pyrimidin-5-yl)-1H-pyrrole, or
3-guanidinocarbonyl-4-methyl-1-(quinolin-3-yl)-1H-pyrrole, or a tautomer thereof or a pharmaceutically acceptable salt of such compound or tautomer.

Further particularly preferred species according to the invention is that of formula 1, which is:
3-guanidinocarbonyl-1-(quinol-2-yl)-1H-pyrrole,
3-guanidinocarbonyl-1-(quinol-4-yl)-1H-pyrrole,
3-guanidinocarbonyl-2-methyl-1-(quinol-4-yl)-1H-pyrrole,
3-guanidinocarbonyl-2-methyl-1-(quinol-2-yl)-1H-pyrrole,
3-guanidinocarbonyl-1-(isoquinol-1-yl)-1H-pyrrole,
3-guanidinocarbonyl-1-(isoquinol-1-yl)-2-methyl-1H-pyrrole,
3-guanidinocarbonyl-1-(quinol-5-yl)-1H-pyrrole,
3-guanidinocarbonyl-1-(quinol-8-yl)-1H-pyrrole,
3-guanidinocarbonyl-1-(isoquinol-4-yl)-1H-pyrrole,
3-guanidinocarbonyl-4-methyl-1-(quinol-4-yl)-1H-pyrrole,
3-guanidinocarbonyl-1-(isoquinol-1-yl)-4-methyl-1H-pyrrole,
3-guanidinocarbonyl-4,5-dimethyl-1-(quinol-4-yl)-1H-pyrrole,
3-guanidinocarbonyl-4-cyclopropyl-1-(quinol-4-yl)-1H-pyrrole,
3-guanidinocarbonyl-4-methyl-1-(quinol-5-yl)-1H-pyrrole,
3-guanidinocarbonyl-4-trifluoromethyl-1-(quinol-4-yl)-1H-pyrrole,
3-guanidinocarbonyl-1-(isoquinol-1-yl)-4-trifluormethyl-1H-pyrrole,
3-guanidinocarbonyl-4-methyl-1-(2-methylquinol-4-yl)-1H-pyrrole,
3-guanidinocarbonyl-1-(2-methylquinol-4-yl)-1H-pyrrole,
3-guanidinocarbonyl-4-methyl-1-(7-chloroquinol-4-yl)-1H-pyrrole,
3-guanidinocarbonyl-1-(7-chloroquinol4-yl)-1H-pyrrole,
3-guanidinocarbonyl-4-methyl-1-(6-fluoroquinol-4-yl)-1H-pyrrole,
3-guanidinocarbonyl-1-(6-fluoroquinol-4-yl)-1H-pyrrole,
3-guanidinocarbonyl-4-methyl-1-(8-fluoroquinol-4-yl)-1H-pyrrole,
3-guanidinocarbonyl-1-(8-fluoroquinol-4-yl)-1H-pyrrole,
3-guanidinocarbonyl-1-(1-cinnolin-4-yl)-1H-pyrrole
3-guanidinocarbonyl 4-methyl-1-(pyrimidin-2-yl)-1H-pyrrole,
3-guanidinocarbonyl-4-methyl-1-(pyridin-2-yl)-1H-pyrrole,
3-guanidinocarbonyl-4-methyl-1-(pyridin-3-yl)-1H-pyrrole,
3-guanidinocarbonyl-4-methyl-1-(pyrimidin-5-yl)-1H-pyrrole, or
3-guanidinocarbonyl-4-methyl-1-(quinolin-3-yl)-1H-pyrrole, or a tautomer thereof or a pharmaceutically acceptable salt of such compound or tautomer.

If the inventive compounds contain one or more centers of asymmetry, these may independently of one another have the S and the R configuration. The compounds may be in the form of optical isomers, of diastereomers, of racemates or of mixtures thereof in any ratio.

The present invention encompasses all tautomeric forms of the compounds of formula I.

The compound of formula I inhibits the cellular sodium-proton antiporter (Na+/H+-exchanger, NHE), in particular the subtype NHE1. Because of the NHE-inhibitory properties. The compound of formula I and/or its pharmaceutically acceptable salt thereof is suitable for the prevention and treatment of diseases caused by activation of or activated NHE, and of diseases caused secondarily by the NHE-related damage.

The use of the compound of formula I relates to the prevention and treatment of acute and chronic diseases in veterinary and human medicine, in particular human medicine.

Thus, the compound of formula I is suitable for the treatment of diseases caused by ischemia and by reperfusion because of its pharmacological properties as antiarrhythmic medicament.

Owing to its cardioprotective component, the compound of formula I and/or its pharmaceutically acceptable salt thereof is outstandingly suitable for infarction prophylaxis and infarction treatment and for the treatment of angina pectoris, in which cases it also preventively inhibits or greatly reduces the pathophysiological process associated with the development of ischemia-induced damage, in particular in the triggering of ischemia-induced cardiac arrhythmias. Because of its protective effect against pathological hypoxic and ischemic situation, the compound of formula I and/or its pharmaceutically acceptable salt thereof can, because of inhibition of the cellular Na+/H+ exchange mechanism, be used as a medicament for the treatment of all acute or chronic ischemia-induced damage or diseases induced primarily or secondarily thereby.

This also relates to its use as medicament for surgical interventions. Thus, the compound of formula I can be used during organ transplantations. It is possible to use the compound both to protect the organs in the donor before and during the removal, to protect removed organs for example during treatment with or storage thereof in physiological bath liquids, and during transfer to the recipient organism.

The compound of formula I is likewise a valuable medicament with a protective effect when performing angioplastic surgical interventions, for example on the heart as well as on peripheral organs and vessels.

It has emerged that the compound of formula I is an effective medicament for life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with compounds of formula I and/or the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication, with such medicaments. The therapeutic benefits of such a cytotoxic therapy can be considerably increased by combination with NHE inhibitors.

In addition, the compound of formula I and/or its pharmaceutically acceptable salt thereof can be used when there is heart-damaging overproduction of thyroid hormones, thyrotoxicosis, or on external supply of thyroid hormones. The compound of formula I and/or its pharmaceutically acceptable salts thereof is, thus, suitable for improving therapy with cardiotoxic medicaments.

In accordance with its protective effect against ischemia-induced damage, the compound of the invention is also suitable as a medicament for the treatment of ischemias of the nervous system, especially of the central nervous system, being suitable, for example, for the treatment of stroke or of cerebral edema.

The compound of formula I and/or its pharmaceutically acceptable salts thereof is also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use a compound of formula I alone or in combination with other substances with antiepileptic activity or antipsychotic active ingredients, or carbonate dehydratase inhibitors, for example, with acetazolamide, and with other inhibitors of NHE or of the sodium-dependent chloride-bicarbonate exchanger (NCBE).

The compound of formula I and/or its pharmaceutically acceptable salt thereof is additionally likewise suitable for the treatment of types of shock such as, allergic, cardiogenic, hypovolemic and bacterial shock.

The compound of formula I and/or its pharmaceutically acceptable salt thereof can likewise be used for the prevention and treatment of thrombotic disorders because it, as an NHE inhibitor, is able to inhibit platelet aggregation itself. It is additionally able to inhibit or prevent the excessive release, occurring after ischemia and reperfusion, of A mediators of inflammation and coagulation, especially of von Willebrand factor and of thrombogenic selectin proteins. It is thus possible to reduce and eliminate the pathogenic effect of significant thrombogenic factors. The compound of formula I can, therefore, be combined with other anticoagulant and/or thrombolytic active ingredients such as recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the compound of formula I with NCBE inhibitors and/or with inhibitors of carbonate dehydratase such as, for example, with acetazolamide, is particularly beneficial.

The compound of formula I and/or its pharmaceutically acceptable salt thereof is additionally distinguished by a strong inhibitory effect on the proliferation of cells, for example, fibroblast proliferation and the proliferation of smooth vascular muscle cells.

The compound of formula I and/or its pharmaceutically acceptable salt thereof is therefore suitable as a valuable therapeutic agent for diseases in which cellular proliferation represents a primary or secondary cause, and can therefore be used as an antiatherosclerotic agent for chronic renal failure, cancers.

It was possible to show that cell migration is inhibited by NHE inhibitors. The compound of formula I and/or its pharmaceutically acceptable salt thereof is, therefore, suitable as a therapeutic agent for diseases in which cell migration represents a primary or secondary cause, such as, cancers with a pronounced tendency to metastasis.

The compound of formula I and/or its pharmaceutically acceptable salt thereof is further distinguished by a retardation or prevention of fibrotic disorders. It is, thus, suitable as an agents for the treatment of cardiac fibroses, and of pulmonary fibrosis, hepatic fibrosis, renal fibrosis and other fibrotic disorders.

It can be used for the treatment of organ hypertrophies and hyperplasias, for example, of the heart and the prostate. It is, therefore, suitable for the prevention and treatment of heart failure (congestive heart failure=CHF) and for the treatment and prevention of prostate hyperplasia or prostate hypertrophy.

Since there is significant elevation in NHE in essential hypertensives, the compound of formula I and/or its pharmaceutically acceptable salt thereof is suitable for the prevention and treatment of high blood pressure and of cardiovascular disorders. In these cases it can be used alone or with a suitable combination and formulation partner for the treatment of high blood pressure and of cardiovascular disorders. Thus, for example, it can be combined with one or more diuretics with a thiazide-like action, loop diuretics, aldosterone and pseudoaldosterone antagonists, such as hydrochlorothiazide, indapamide, polythiazide, furosemide, piretamide, torasemide, bumetamide, amiloride, triamterene, spironolactone or eplerone. The compound of formula I and/or its pharmaceutically acceptable salt thereof can further be used in combination with calcium channel blockers such as verapamil, diltiazem, amLodipine or nifedipine, and with ACE inhibitors such as ramipril, enalapril, lisinopril, fosinopril or captopril. Further beneficial combination partners are also beta-blockers such as metoprolol, albuterol etc., antagonists of the angiotensin receptor and its receptor subtypes such as losartan, irbesartan, valsartan; omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has emerged that the compound of formula I and/or its pharmaceutically acceptable salt thereof has a significant antiinflammatory effect and can thus be used as an antiinflammatory drug. Inhibition of the release of mediators of inflammation is noteworthy in this connection. The compound can, thus, be used alone or in combination with an antiinflammatory drug for the prevention or treatment of chronic and acute inflammatory disorders. Combination partners advantageously used are steroidal and non-steroidal antiinflammatory drugs. The compound of formula I and/or its pharmaceutically acceptable salt thereof can also be used for the treatment of disorders caused by protozoa, of malaria and of coccidiosis in poultry.

It has additionally been found that compound of formula I and/or its pharmaceutically acceptable salts thereof shows a beneficial effect on serum lipoproteins. It is generally acknowledged that blood fat levels which are too high, called hyperlipoproteinemias, represent an essential risk factor for the development of arteriosclerotic vascular lesions, especially coronary heart disease. The reduction of elevated serum lipoproteins, therefore, has exceptional importance for the prophylaxis and regression of atherosclerotic lesions. Besides the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has now been found that NHE1 inhibitors show valuable therapeutically utilizable properties in relation to influencing the serum lipid levels. Thus, they significantly reduce the elevated serum concentrations of LDL and VLDL as are to be observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the compound of formula I and/or its pharmaceutically acceptable salt thereof leads to a marked reduction in the infarctions induced by metabolic abnormalities and, in particular, to a significant reduction in the induced infarct size and the severity thereof. Said compound is, therefore, advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia-induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of a compound of formula I and/or the pharmaceutically acceptable salt thereof with an active ingredient lowering the blood fat levels, preferably with an HMG-CoA reductase inhibitor (for example lovastatin or pravastatin), the latter bringing about a hypolipidemic effect and thus increasing the hypolipidemic properties of the compound of formula I and/or the pharmaceutically acceptable salt thereof, proves to be a favorable combination with enhanced effect and reduced use of active ingredients.

Thus, compounds of formula I and/or the pharmaceutically acceptable salts thereof lead to effective protection against endothelial damage of various origins. This protection of the vessels against the syndrome of endothelial dysfunction means that the compounds of formula I and/or the pharmaceutically acceptable salts thereof are valuable medicaments for the prevention and treatment of coronary vasospasms, peripheral vascular diseases, in particular intermittent claudication, atherogenesis and atherosclerosis, left ventricular hypertrophy and dilated cardiomyopathy and thrombotic disorders.

It has additionally been found that compounds of formula I and/or the pharmaceutically acceptable salts thereof are suitable in the treatment of non-insulin-dependent diabetes (NIDDM), with the insulin resistance being restrained. It may in this connection be beneficial, to enhance the antidiabetic activity and quality of the effect of the compounds of the invention, to combine them with a biguanide such as metformin with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Besides the acute antidiabetic effects, the compounds of formula I and/or the pharmaceutically acceptable salts thereof counteract the development of late complications of diabetes and can therefore be used as medicaments for the prevention and treatment of late damage from diabetes, such as diabetic nephropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin should be particularly important in this connection.

The NHE inhibitors of the invention of formula I and/or the pharmaceutically acceptable salts thereof show, besides the protective effects against acute ischemic events and the subsequent equally acutely stressing reperfusion events, also direct therapeutically utilizable effects against diseases and disorders of the entire mammalian organism which are associated with the manifestations of the chronically progressive aging process and which occur independently of acute hypoperfusion states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. The compounds of formula I and/or the pharmaceutically acceptable salts thereof are thus outstandingly suitable for the treatment and prevention of the age-related progression in endothelial dysfunction, especially of intermittent claudication.

An example of another variable characterizing the aging process is the decline in the contractability of the heart and the decline in the adaptation of the heart to a required pumping output of the heart. This diminished efficiency of the heart as a consequence of the aging process is in most cases connected with a dysfunction of the heart that is caused inter alia by deposition of connective tissue in the myocardial tissue. This deposition of connective tissue is characterized by an increase in the weight of the heart, by an enlargement of the heart and by restrictive cardiac function. It was surprising that it was possible almost completely to inhibit such aging of the heart organ. The compounds of formula I and/or the pharmaceutically acceptable salts thereof are thus outstandingly suitable for the treatment and prevention of heart failure, of congestive heart failure (CHF).

Whereas preceding patents and patent applications have claimed the treatment of various forms of cancer which have already occurred, it was now extremely surprising that not only is it possible to cure a cancer which has already occurred through inhibition of proliferation, but there is also prevention and highly significant retardation of the age-related incidence of cancer through NHE inhibitors. A particularly noteworthy finding is that the disorders, occurring as a result of aging, of all organs and not only certain types of cancer are suppressed or occur with a highly significant delay. The compounds of formula I and/or the pharmaceutically acceptable salts thereof are thus outstandingly suitable for the treatment and, in particular, the prevention of age-related types of cancer.

There is now found to be not only a delay, shifted highly significantly in time and beyond the normal statistical extent, in the occurrence of age-related disorders of all the organs investigated, including the heart, vessels, liver etc., and a highly significant delay in cancer of the elderly. On the contrary, there is also surprisingly a prolongation of life to an extent which has to date been achievable by no other group of medicaments or by any natural products. This unique effect of NHE inhibitors also makes it possible, besides the use of the active ingredients alone on humans and animals, to combine these NHE inhibitors with other active principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, the combination with dietary measures can take place for example with appetite suppressants. It is likewise possible to consider a combination with hypotensive medicaments such as with ACE inhibitors, angiotensin receptor antagonists, diuretics, $Ca^{2+}$ antagonists etc. or with metabolism-normalizing medicaments such as cholesterol-lowering agents.

The compounds of formula I and/or the pharmaceutically acceptable salts thereof are thus outstandingly suitable for the prevention of age-related tissue changes and for prolonging life while retaining a high quality of life.

The compounds of the invention are effective inhibitors of the cellular sodium-proton antiporter (Na/H exchanger) which in a large number of disorders (essential hypertension, atherosclerosis, diabetes etc.) is also increased in cells which are readily amenable to measurements, such as, for example, in erythrocytes, platelets or leucocytes. The compounds according to the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

The present invention also relates to processes for synthesising 3-guanidinocarbonyl-1-heteroaryl-pyrrole derivatives of formula (I).

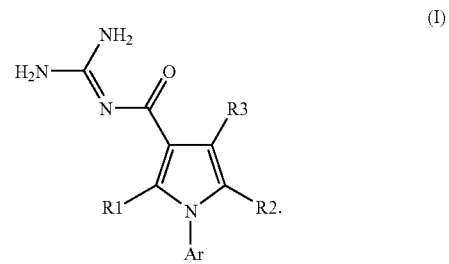

The compounds of the general formula (I) can be prepared from the 3-carboxy-1H-pyrroles of the general formula (II) in accordance with the following general synthetic scheme:

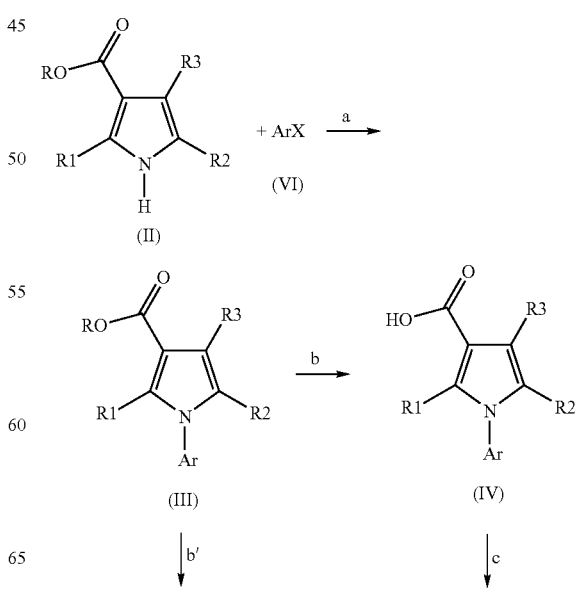

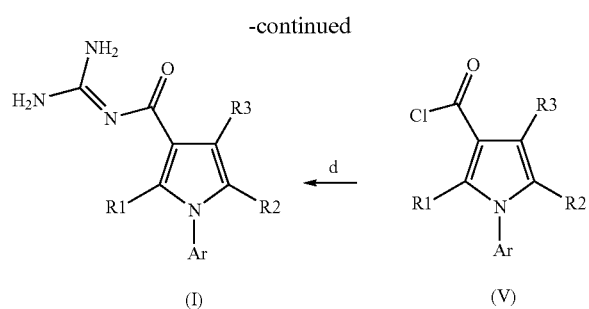

The general synthetic scheme is as follows:
a) a heteroaryl halide ArX of formula (VI) is reacted with a 3-alkoxycarbonyl-1H-pyrrole of formula (II)
b) the obtained 3-alkoxycarbonyl-1-heteroaryl-1H-pyrrole of formula (III) is saponified
c) the 3-carboxy-1-heteroaryl-1H-pyrrole of formula(IV) is converted in the acid chloride of formula (V)
d) the obtained product of formula (V) is reacted with guanidine, alternatively the compound of formula I can be obtained as follows
a) a heteroaryl halide ArX of formula (VI) is reacted with a 3-alkoxycarbonyl-1H-pyrrole of formula (II)
b') the obtained 3-alkoxycarbonyl-1-heteroaryl-1H-pyrrole (III) is reacted with guanidine, wherein in the compounds of formula II, III, IV, V, and VI Ar and $R_1$ to $R_3$ are defined as in the compounds of formula I,
X is F, Cl, Br or I and,
R is $C_1$–$C_6$ alkyl.

The product is isolated and is optionally converted into a pharmaceutically acceptable salt.

The compounds of the general formulae (II) and (VI) that are not commercially available can be obtained by application or adaptation of the methods described in the literature, for example by Leusen A. M. et al., Tetrahedron Lett., (1972), (52), 5337–40, or Korte F. et al., Chem. Ber., (1962), (95), 307–18.

Reaction a) between a suitable 3-alkoxycarbonyl-1H-pyrrole of formula (II) and a suitable heteroaryl halide ArX of formula (VI) is preferably performed under an inert atmosphere (for example under nitrogen or under argon) in a basic medium, for example in the presence of sodium hydride, and optionally of copper powder, in an inert solvent, such as dimethylformamide, at a temperature of between 20° C. and the boiling point of the reaction medium, preferably at a temperature in the region of 140° C.

Alternatively, reaction a) between a suitable 3-alkoxycarbonyl-1H-pyrrole of formula (II) and a suitable heteroaryl halide ArX of formula (VI) can be performed preferably under an inert atmosphere (for example under nitrogen or under argon) in a basic medium, for example in the presence of potassium carbonate, in an inert solvent, such as dimethyl sulphoxide, at a temperature of between 20° C. and the boiling point of the reaction medium, preferably at a temperature in the region of 100° C. Reaction a) between a suitable 3-alkoxycarbonyl-1H-pyrrole of formula (II) and a suitable heteroaryl halide ArX of formula (VI) can also be performed preferably under an inert atmosphere (for example under nitrogen or under argon) in a basic medium, for example in the presence of potassium orthophosphate, copper iodide and trans-1,2-cyclohexanediamine, in an inert solvent, such as a mixture of 1,4-dioxane and n-dodecane, at a temperature of between 20° C. and the boiling point of the reaction medium, preferably at a temperature in the region of 100° C.

Reaction (b) is generally performed according to the usual methods that do not affect the rest of the molecule, in particular by applying methods described by T. W. Greene and P. G. M. Wuts, Protective Groups in Organic Synthesis (2nd ed.), A. Wiley, Interscience Publication (1991), or by McOmie, Protective Groups in Organic Chemistry, Plenum Press (1973), or by Bradford P. Mundy and Michael G. Ellerd, Name Reactions and Reagents in Organic Synthesis, A. Wiley, Interscience Publication (1988). For example, the saponification reaction b) of a suitable 3-alkoxycarbonyl-1-heteroaryl-1H-pyrrole of formula (III) is performed in a basic medium, for example in the presence of lithium hydroxide monohydrate, in an inert solvent, such as a mixture of tetrahydrofuran and water, at a temperature of between 20° C. and the boiling point of the reaction medium, preferably at the reflux point of the reaction medium.

Reaction c) is generally performed according to the usual methods that do not affect the rest of the molecule, in particular by applying methods described by Bradford P. Mundy and Michael G. Ellerd, Name Reactions and Reagents in Organic Synthesis, A. Wiley, Interscience Publication (1988). For example, the reaction c) for the formation of the acid chloride of a suitable 3-carboxy-1-heteroaryl-1H-pyrrole of formula (IV) is preferably performed under an inert atmosphere (for example under nitrogen or under argon) in the presence of oxalyl chloride in an inert solvent, such as dichloromethane, at a temperature of between 20° C. and the boiling point of the reaction medium, preferably at a temperature in the region of 20° C., or in the presence of sulphinyl chloride in an inert solvent, such as chloroform, at a temperature of between 20° C. and the boiling point of the reaction medium, preferably at the reflux point of the reaction medium.

Reaction d) between a suitable 3-chlorocarbonyl-1-heteroaryl-1H-pyrrole of formula (V) and guanidine is preferably performed under an inert atmosphere (for example under nitrogen or under argon) in an inert solvent, such as 1,2-dimethoxyethane, tetrahydrofuran or dichloromethane, at a temperature in the region of 20° C.

Reaction b') between a suitable 3-alkoxycarbonyl-1-heteroaryl-1H-pyrrole of formula (III) and guanidine hydrochloride is preferably performed under an inert atmosphere (for example under nitrogen or under argon) in the presence of a base, such as potassium tert-butoxide, in an inert solvent, such as dimethylformamide, at a temperature of between 20° C. and the boiling point of the reaction medium, preferably at a temperature in the region of 100° C.

The compounds of formula (I) are isolated and can be purified by the usual known methods, for example by crystallisation, chromatography or extraction.

The compounds of formula I can optionally be converted into addition salts with an inorganic or organic acid by reacting with such an acid in a solvent, e.g. an organic solvent such as an alcohol, a ketone, an ether or a chlorinated solvent. These salts also form part of the invention. Examples of pharmaceutically acceptable salts that can be mentioned include the following salts: benzenesulphonate, hydrobromide, hydrochloride, acetate, citrate, ethanesulphonate, fumarate, gluconate, iodate, maleate; isethionate, methanesulphonate, methylenebis(β-oxynaphthoate), nitrate, oxalate, pamoate, phosphate, salicylate, succinate, sulphate, tartrate, theophyllinacetate and p-toluenesulphonate.

If the compounds contain an acid group, they are capable of forming salts with bases, for example alkali metal salts, preferably sodium or potassium salts, or ammonium salts, for example salts with ammonia or organic amines or amino acids. They can also be present as zwitterions.

EXAMPLES

Example 1 a) 3-Guanidinocarbonyl-1-(quinol-2-yl)-1H-pyrrole hydrochloride

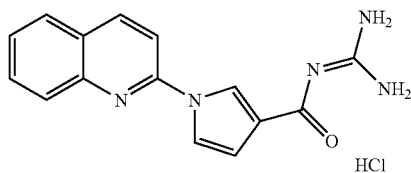

1.57 g (14 mmol) of potassium tert-butoxide are added at 20° C. under an argon atmosphere to 1.6 g (16.8 mmol) of guanidine hydrochloride dissolved in 35 mL of dimethylformamide. After stirring at 20° C. for 1 hour, 0.7 g (2.8 mmol) of 3-methoxycarbonyl-1-(quinol-2-yl)-1H-pyrrole, dissolved in 7 mL of dimethylformamide, is added. After stirring at 100° C. for 11 hours, the reaction mixture is cooled and then concentrated to dryness under reduced pressure (2.7 kPa) to give an oil which is allowed to crystallise from 10 mL of water for 1 hour. After filtering off and air-drying the solid residue, 0.84 g of a beige-coloured solid is obtained, which solid is purified by flash chromatography [eluent: dichloromethane/methanol/acetonitrile (90/5/5 by volume)]. After concentrating the fractions under reduced pressure, a white solid is obtained, which solid is recrystallised under hot conditions from 30 mL of methanol to give 0.352 g of 3-guanidinocarbonyl-1-(quinol-2-yl)-1H-pyrrole hydrochloride in the form of a white solid melting at 258° C. Mass spectrum (DCI): m/e 280 (M+H)+.

b) 3-Methoxycarbonyl-1-(quinol-2-yl)-1H-pyrrole 1.73 g (12.5 mmol) of potassium carbonate are added at 20° C. under an argon atmosphere to 0.625 g (5 mmol) of 3-methoxycarbonyl-1H-pyrrole and 0.82 g (5 mmol) of 2-chloroquinoline dissolved in 10 mL of dimethyl sulphoxide. After stirring at 100° C. for 23 hours, the reaction mixture is poured into 30 mL of water and is then allowed to crystallise at 20° C. for 1 hour. After filtering off and air-drying the solid residue, 0.83 g of 3-methoxycarbonyl-1-(quinol-2-yl)-1H-pyrrole is obtained in the form of a beige-coloured solid melting at 136° C.

c) 3-Methoxycarbonyl-1H-pyrrole can be prepared as described by Leusen, A. M. et al., Tetrahedron Letters (1972), (52), 5337–5340, which is incorporated by reference herein.

Example 2 a) 3-Guanidinocarbonyl-1-(quinol-4-yl)-1H-pyrrole dihydrochloride

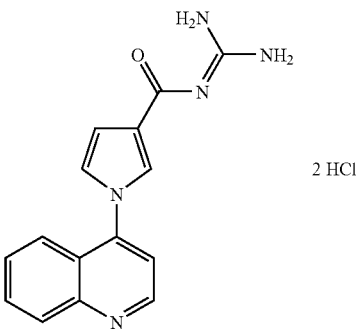

1.4 g (12.5 mmol) of potassium tert-butoxide are added at 20° C. under an argon atmosphere to 1.43 g (15 mmol) of guanidine hydrochloride dissolved in 37.5 mL of dimethylformamide. After stirring at 20° C. for 1 hour, 0.64 g (2.5 mmol) of 3-methoxycarbonyl-1-(quinol-4-yl)-1H-pyrrole is added. After stirring at 100° C. for 8 hours, the reaction mixture is cooled and then concentrated to dryness under reduced pressure (2.7 kPa) to give an oil which is allowed to crystallise from 10 mL of water for 0.5 hour. After filtering off and air-drying the solid residue, 0.72 g of a beige-coloured solid is obtained, which solid is purified by flash chromatography [eluent: dichloromethane/methanol/acetonitrile (90/5/5 by volume) and then chloroform/methanol/20% aqueous ammonia (24/6/0.5 by volume)]. After concentrating the fractions under reduced pressure, 0.72 g of a white solid is obtained, which solid is triturated in 30 mL of N hydrochloric acid. After concentrating to dryness under reduced pressure (2.7 kPa), the residue is recrystallised under hot conditions from 20 mL of methanol to give 0.515 g of 3-guanidinocarbonyl-1-(quinol-4-yl)-1H-pyrrole dihydrochloride in the form of a white solid melting at 244° C. IR spectrum (KBr): 3303, 3108, 1694, 1697, 1597, 1498, 1285, 1255 and 753 cm$^{-1}$.

b) 3-Methoxycarbonyl-1-(quinol-4-yl)-1H-pyrrole 1.73 g (12.5 mmol) of potassium carbonate are added at 20° C. under an argon atmosphere to 0.625 g (5 mmol) of 3-methoxycarbonyl-1H-pyrrole and 0.82 g (5 mmol) of 4-chloroquinoline dissolved in 10 mL of dimethyl sulphoxide. After stirring at 100° C. for 23 hours, the reaction mixture is poured into 30 mL of water and then allowed to crystallise at 20° C. for 1 hour. After filtering off and air-drying the solid residue, 0.75 g of 3-methoxycarbonyl-1-(quinol-4-yl)-1H-pyrrole is obtained in the form of a beige-coloured solid melting at 156° C.

c) 3-Methoxycarbonyl-1H-pyrrole can be prepared as described by Leusen, A. M. et al., Tetrahedron Letters (1972), (52), 5337–5340, which is incorporated by reference herein.

Example 3 a) 3-Guanidinocarbonyl-2-methyl-1-(quinol-4-yl)-1H-pyrrole dihydrochloride

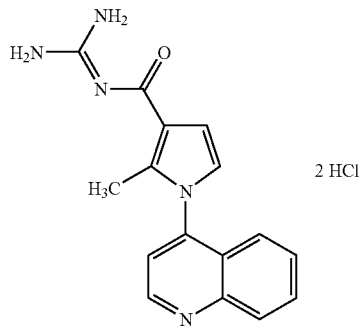

0.882 (38.4 mmol) of sodium is added at 20° C. under an argon atmosphere to 50 mL of methanol. After complete dissolution, 3.45 g of (36.2 mmol) of guanidine hydrochloride are added. After stirring at 20° C. for 0.5 hour, the reaction mixture is filtered under an argon atmosphere. The filtrate is concentrated to dryness under reduced pressure (2.7 kPa) to give a residue that is dissolved in 40 mL of 1,2-dimethoxyethane. 2.2 g of 3-chlorocarbonyl-2-methyl-1-(quinol-4-yl)-1H-pyrrole hydrochloride, dissolved in 10 mL of 1,2-dimethoxyethane, are then added at 20° C. under an argon atmosphere. After stirring at 20° C. for 7 hours, the reaction mixture is concentrated to dryness under reduced pressure (2.7 kPa) to give a residue that is triturated in 100 mL of water for 15 hours. After filtering off and drying under reduced pressure (2.7 kPa) at 40° C., 2.1 g of a beige-coloured solid are obtained, which solid is purified by flash chromatography [eluent: dichloromethane/methanol/acetonitrile (86/7/7 by volume) and then dichloromethane/methanol/20% aqueous ammonia (96/24/2 by volume)]. After concentrating the fractions under reduced pressure, 1.62 g of a beige-coloured solid are obtained, which solid is triturated in 50 mL of N hydrochloric acid for 2 hours. After filtering, the filtrate is concentrated to dryness under reduced pressure (2.7 kPa) to give a residue which is recrystallised under hot conditions from 40 mL of methanol to give 1.32 g of 3-guanidinocarbonyl-2-methyl-1-(quinol-4-yl)-1H-pyrrole dihydrochloride in the form of a yellow solid melting at 240° C.

IR spectrum (KBr): 3382, 3084, 2484, 1686, 1634, 1597, 1559, 1494, 1425, 1312, 1284, 1191 and 856 cm$^{-1}$.

b) 3-Chlorocarbonyl-2-methyl-1-(quinol-4-yl)-1H-pyrrole hydrochloride 11.8 mL (134.8 mmol) of oxalyl chloride are added at 20° C. under an argon atmosphere to 2.09 g (7.24 mmol) of 3-carboxy-2-methyl-1-(quinol-4-yl)-1H-pyrrole dissolved in 150 mL of dichloromethane. After stirring at 20° C. for 16 hours, the reaction mixture is concentrated to dryness under reduced pressure (2.7 kPa) to give 2.2 g of 3-chlorocarbonyl-2-methyl-1-(quinol-4-yl)-1H-pyrrole hydrochloride in the form of an orange-coloured solid which is used directly in the following step.

c) 3-Carboxy-2-methyl-1-(quinol-4-yl)-1H-pyrrole 2.226 g (53 mmol) of lithium hydroxide monohydrate, in portions of 0.742 g every 24 hours, are added at 20° C. to 2.48 g (8.4 mmol) of 3-ethoxycarbonyl-2-methyl-1-(quinol-4-yl)-1H-pyrrole dissolved in 75 mL of tetrahydrofuran and 75 mL of water. After stirring at reflux for 72 hours, the reaction mixture is concentrated to dryness under reduced pressure (2.7 kPa) to give a residue which is taken up in 40 mL of water and then triturated with 10 mL of 5N hydrochloric acid for 0.2 hour. After filtering off and drying the solid residue under reduced pressure (2.7 kPa) at 40° C., 2.09 g of 3-carboxy-2-methyl-1-(quinol-4-yl)-1H-pyrrole are obtained in the form of a pinkish solid. Mass spectrum (EI): m/e 252 (M$^{+\cdot}$), m/e 207.

d) 3-Ethoxycarbonyl-2-methyl-1-(quinol-4-yl)-1H-pyrrole 2.75 g (17.9 mmol) of 3-ethoxycarbonyl-2-methyl-1H-pyrrole are added at 20° C. under an argon atmosphere to 0.756 g (18.9 mmol) of sodium hydride, at 60% by weight in liquid petroleum jelly, suspended in 12 mL of dimethylformamide. After stirring at 20° C. for 0.2 hour, 0.114 g (1.79 mmol) of copper powder and 2.35 mL (17.9 mmol) of 4-chloroquinoline are added. After stirring at 140° C. for 48 hours, the reaction mixture is filtered and the filtrate is concentrated to dryness under reduced pressure (2.7 kPa) to give a residue which is taken up in 100 mL of water and then extracted with 3 times 70 mL of ethyl acetate. The organic phases are combined, dried over anhydrous magnesium sulphate, filtered and then concentrated to dryness under reduced pressure (2.7 kPa) to give 5.2 g of a brown oil which is purified by flash chromatography [eluent: dichloromethane/ethyl acetate (97/3 by volume)]. After concentrating the fractions under reduced pressure (2.7 kPa), 3 g of 3-ethoxycarbonyl-2-methyl-1-(quinol-4-yl)-1H-pyrrole are obtained in the form of an orange-coloured oil. Mass spectrum (EI): m/e 280 (M$^{+\cdot}$), m/e 251, m/e 235.

Example 4 a) 3-Guanidinocarbonyl-2-methyl-1-(quinol-2-yl)-1H-pyrrole hydrochloride

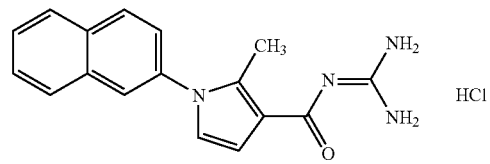

0.795 g (33.1 mmol) of sodium is added at 20° C. under an argon atmosphere to 30 mL of methanol. After complete dissolution, 2.97 g (31.2 mmol) of guanidine hydrochloride are added. After stirring at 20° C. for 0.5 hour, the reaction mixture is filtered under an argon atmosphere. The filtrate is concentrated to dryness under reduced pressure (2.7 kPa) to give a residue that is dissolved in 15 mL of 1,2-dimethoxyethane. 2 g of 3-chlorocarbonyl-2-methyl-1-(quinol-2-yl)-

1H-pyrrole hydrochloride, suspended in 15 mL of 1,2-dimethoxyethane, are then added at 20° C. under an argon atmosphere. After stirring at 20° C. for 8 hours, the reaction mixture is concentrated to dryness under reduced pressure (2.7 kPa) to give a residue that is triturated in 100 mL of water for 16 hours. After filtering off and drying the solid residue under reduced pressure (2.7 kPa), a residue is obtained, which residue is purified by flash chromatography [eluent: dichloromethane/methanol/acetonitrile (86/7/7 by volume) and then dichloromethane/methanol/20% aqueous ammonia (96/24/2 by volume)]. After concentrating the fractions under reduced pressure, a beige-coloured solid is obtained, which solid is triturated in 100 mL of N hydrochloric acid for 15 hours. After filtration, the solid residue is recrystallised under hot conditions from 30 mL of methanol to give 0.82 g of 3-guanidinocarbonyl-2-methyl-1-(quinol-2-yl)-1H-pyrrole hydrochloride in the form of a pinkish solid melting at 250° C. Mass spectrum (EI): m/e 293 (M+·), m/e 206 (base peak).

b) 3-Chlorocarbonyl-2-methyl-1-(quinol-2-yl)-1H-pyrrole hydrochloride 10 mL (114.2 mmol) of oxalyl chloride are added at 20° C. under an argon atmosphere to 1.8 g (6.25 mmol) of 3-carboxy-2-methyl-1-(quinol-2-yl)-1H-pyrrole dissolved in 120 mL of dichloromethane. After stirring at 20° C. for 16 hours, the reaction mixture is concentrated to dryness under reduced pressure (2.7 kPa) to give 2 g of 3-chlorocarbonyl-2-methyl-1-(quinol-2-yl)-1H-pyrrole hydrochloride in the form of a beige-coloured solid which is used directly in the following step.

c) 3-Carboxy-2-methyl-1-(quinol-2-yl)-1H-pyrrole 3.9 g (93 mmol) of lithium hydroxide monohydrate, portionwise every 24 hours, are added at 20° C. to 1.9 g (6.78 mmol) of 3-ethoxycarbonyl-2-methyl-1-(quinol-2-yl)-1H-pyrrole dissolved in 50 mL of tetrahydrofuran and 50 mL of water. After stirring at reflux for 72 hours, the reaction mixture is concentrated to dryness under reduced pressure (2.7 kPa) to give a residue that is taken up in 75 mL of water. The pH of the aqueous phase is adjusted to 2 by addition of concentrated hydrochloric acid. After stirring for 1 hour, the aqueous phase is filtered and the solid residue is dried under reduced pressure (2.7 kPa) at 40° C. to give 1.9 g of 3-carboxy-2-methyl-1-(quinol-2-yl)-1H-pyrrole in the form of a beige-coloured solid.

d) 3-Ethoxycarbonyl-2-methyl-1-(quinol-2-yl)-1H-pyrrole 2.75 g (17.9 mmol) of 3-ethoxycarbonyl-2-methyl-1H-pyrrole are added at 20° C. under an argon atmosphere to 0.756 g (18.9 mmol) of sodium hydride, at 60% by weight in liquid petroleum jelly, suspended in 12 mL of dimethylformamide. After stirring at 20° C. for 0.2 hour, 0.114 g (1.79 mmol) of copper powder and 2.93 g (17.9 mmol) of 2-chloroquinoline are added. After stirring at 140° C. for 48 hours, the reaction mixture is filtered and the filtrate is concentrated to dryness under reduced pressure (2.7 kPa) to give a residue which is taken up in 100 mL of water and then extracted with 4 times 50 mL of ethyl acetate. The organic phases are combined, dried over anhydrous magnesium sulphate, filtered and then concentrated to dryness under reduced pressure (2.7 kPa) to give 6 g of an oil, which oil is purified by flash chromatography [eluent: cyclohexane/ethyl acetate (8/2 by volume)]. After concentrating the fractions under reduced pressure (2.7 kPa), 2.2 g of 3-ethoxycarbonyl-2-methyl-1-(quinol-2-yl)-1H-pyrrole are obtained in the form of a yellow oil. Mass spectrum (EI): m/e 280 (M+·), m/e 251, m/e 206.

Example 5 a) 3-Guanidinocarbonyl-1-(isoquinol-1-yl)-1H-pyrrole hydrochloride

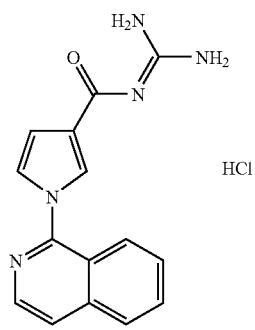

0.255 g (11 mmol) of sodium is added at 20° C. under an argon atmosphere to 50 mL of methanol. After complete dissolution, 1.05 g (11 mmol) of guanidine hydrochloride are added. After stirring at 20° C. for 0.25 hour, the reaction mixture is filtered under an argon atmosphere. The filtrate is concentrated to dryness under reduced pressure (2.7 kPa) to give a residue that is dissolved in 10 mL of tetrahydrofuran. 0.650 g of 3-chlorocarbonyl-1-(isoquinol-1-yl)-1H-pyrrole hydrochloride, dissolved in 20 mL of tetrahydrofuran, is then added at 20° C. under an argon atmosphere. After stirring at 20° C. for 17 hours, the reaction mixture is filtered and the filtrate is concentrated to dryness under reduced pressure (2.7 kPa) to give a residue which is triturated in 10 mL of water for 1 hour. After filtering off, the solid residue is air-dried to give 0.4 g of a beige-coloured solid which is triturated in 25 mL of N hydrochloric acid for 1 hour. After concentrating to dryness under reduced pressure (2.7 kPa), the solid residue is washed with 3 times 5 mL of methanol and twice 10 mL of pentane and then air-dried. 0.25 g of 3-guanidinocarbonyl-1-(isoquinol-1-yl)-1H-pyrrole hydrochloride is thus obtained in the form of a white solid melting at a temperature of greater than 250° C. IR spectrum (KBr): 3356, 3127, 1686, 1626, 1497, 1411, 1330, 1274, 752 and 669 cm$^{-1}$.

b) 3-Chlorocarbonyl-1-(isoquinol-1-yl)-1H-pyrrole hydrochloride 0.4 mL (4.5 mmol) of oxalyl chloride is added at 20° C. under an argon atmosphere to 0.58 g (2.2 mmol) of 3-carboxy-1-(isoquinol-1-yl)-1H-pyrrole dissolved in 45 mL of dichloromethane. After stirring at 20° C. for 0.5 hour, the reaction mixture is concentrated to dryness under reduced pressure (2.7 kPa) to give 0.65 g of 3-chlorocarbonyl-1-(isoquinol-1-yl)-1H-pyrrole hydrochloride in the form of a beige-coloured solid which is used directly in the following step.

c) 3-carboxy-1-(isoquinol-1-yl)-1H-pyrrole 0.237 g (5.65 mmol) of lithium hydroxide monohydrate is added at 20° C. to 0.57 g (2.26 mmol) of 3-methoxycarbonyl-1-(isoquinol-1-yl)-1H-pyrrole dissolved in 15 mL of tetrahydrofuran and 15 mL of water. After stirring at reflux for 2 hours, the reaction mixture is concentrated to dryness under reduced pressure (2.7 kPa) to give a residue which is taken up in 5 mL of water and then triturated with 5.65 mL of N hydrochloric acid for 1 hour. The aqueous phase is filtered and the solid residue is washed with twice 5 mL of water and then air-dried to give 0.58 g of 3-carboxy-1-(isoquinol-1-yl)-1H-pyrrole in the form of a white solid. Mass spectrum (EI): m/e 238 (M$^{+\cdot}$), m/e 193.

d) 3-Methoxycarbonyl-1-(isoquinol-1-yl)-1H-pyrrole 1.04 g (7.5 mmol) of potassium carbonate are added at 20° C. under an argon atmosphere to 0.376 g (3 mmol) of 3-methoxycarbonyl-1H-pyrrole and 0.49 g (3 mmol) of 1-chloroisoquinoline dissolved in 6 mL of dimethyl sulphoxide. After stirring at 100° C. for 22 hours, the reaction mixture is poured into 15 mL of water and is then allowed to crystallise for 1 hour at 20° C. After filtering the reaction mixture and air-drying the solid residue, 0.67 g of 3-methoxycarbonyl-1-(isoquinol-1-yl)-1H-pyrrole is obtained in the form of a beige-coloured solid melting at 86° C. Mass spectrum (EI): m/e 252 (M$^{+\cdot}$), m/e 221.

Example 6 a) 3-Guanidinocarbonyl-1-(quinol-5-yl)-1H-pyrrole

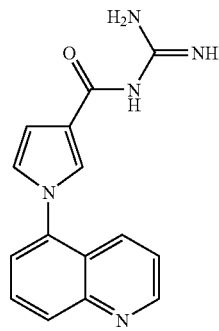

0.9 g (9.42 mmol) of guanidine hydrochloride is added to a solution of 0.51 g (9.44 mmol) of sodium methoxide in 15 mL of methanol at a temperature in the region of 22° C. under an argon atmosphere. After stirring at a temperature in the region of 22° C. for 2 hours, the solvent is evaporated off under reduced pressure (2.7 kPa). The residue, placed under an argon atmosphere, is taken up in 20 mL of a tetrahydrofuran/dichloromethane (1/1 by volume) mixture and then 0.55 g (1.88 mmol) of 3-chlorocarbonyl-1-(quinol-5-yl)-1H-pyrrole hydrochloride, dissolved in 5 mL of the same tetrahydrofuran/dichloromethane mixture, is added thereto. After stirring at a temperature in the region of 22° C. for 15 hours, the reaction mixture is concentrated to dryness under reduced pressure (2.7 kPa). The residue is triturated with water, filtered and taken up under hot conditions in 7 mL of ethanol. The insoluble material is then filtered off and discarded, and the filtrate is cooled to a temperature in the region of 22° C. The crystals formed are filtered off and dried under vacuum (2.7 kPa), to give 0.165 g of 3-guanidinocarbonyl-1-(quinol-5-yl)-1H-pyrrole in the form of a white solid melting at 260° C. Mass spectrum (EI): m/e 279 (M$^{+\cdot}$), m/e 221.

b) 3-Chlorocarbonyl-1-(quinol-5-yl)-1H-pyrrole hydrochloride 0.5 mL (5.73 mmol) of oxalyl chloride is added to a solution, cooled to a temperature in the region of 5° C., of 0.42 g (1.76 mmol) of 3-carboxy-1-(quinol-5-yl)-1H-pyrrole in 10 mL of dichloromethane under an argon atmosphere. After stirring at a temperature in the region of 22° C. for 15 hours, concentrating the reaction mixture to dryness under reduced pressure (2.7 kPa) gives 0.55 g of 3-chlorocarbonyl-1-(quinol-5-yl)-1H-pyrrole hydrochloride in the form of a cream-coloured solid which is used directly in the following step.

c) 3-Carboxy-1-(quinol-5-yl)-1H-pyrrole 0.36 g (8.58 mmol) of lithium hydroxide monohydrate and 20 mL of water are added to a solution at a temperature in the region of 22° C. of 0.5 g (1.98 mmol) of 3-methoxycarbonyl-1-(quinol-5-yl)-1H-pyrrole in 20 mL of tetrahydrofuran. After stirring at the reflux point of the solvent for 15 hours, the reaction mixture is concentrated to dryness under reduced pressure (2.7 kPa) and the residue is taken up in water. The resulting solution is adjusted to pH 7 using N hydrochloric acid and then it is extracted with ethyl acetate. The organic phase is washed with a saturated sodium chloride solution, dried over magnesium sulphate, filtered and concentrated to dryness under reduced pressure (2.7 kPa). 0.42 g of 3-carboxy-1-(quinol-5-yl)-1H-pyrrole is thus obtained in the form of a white solid. IR spectrum (KBr): 3423, 3105, 1665, 1536, 1275, 1188, 1107, 965 and 796 cm$^{-1}$.

d) 3-Methoxycarbonyl-1-(quinol-5-yl)-1H-pyrrole 10 mL of 1,4-dioxane, 0.32 mL of n-dodecane, 2.2 g (8.63 mmol) of 5-iodoquinoline and 0.770 mL (6.41 mmol) of trans-1,2-cyclohexanediamine are added at a temperature in the region of 22° C. under an argon atmosphere to 0.8 g (6.39 mmol) of 3-methoxycarbonyl-1H-pyrrole, 2.85, g (13.43 mmol) of potassium orthophosphate and 0.08 g (0.42 mmol) of copper iodide. After stirring at a temperature in the region of 100° C. for 15 hours, the reaction mixture is concentrated to dryness under reduced pressure (2.7 kPa). The residue is diluted with 100 mL of ethyl acetate and the solution obtained is washed with twice 100 mL of water and then with 25 mL of saturated aqueous sodium chloride solution. After separating the phases by settling, the organic phase is dried over anhydrous magnesium sulphate, filtered and concentrated to dryness under reduced pressure (2.7 kPa) to give 2.2 g of an orange-coloured oil which is purified by flash chromatography [eluent: cyclohexane/ethyl acetate (80/20 by volume)]. After concentrating the fractions under reduced pressure, 0.4 g of 3-methoxycarbonyl-1-(quinol-5-yl)-1H-pyrrole is obtained in the form of a yellow solid. Mass spectrum (EI): EI: m/e 252 (M+·), m/e 221.

e) 5-Iodoquinoline can be prepared according to the method described by M. Istrati, C. R. Hebd. Séances Acad. Sci. (1898), 127, 521, which is incorporated by reference herein.

Example 7 a) 3-Guanidinocarbonyl-1-(quinol-8-yl)-1H-pyrrole

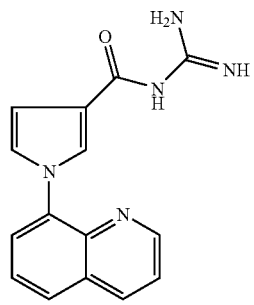

0.681 g (7.13 mmol) of guanidine hydrochloride is added to a solution of 0.385 g (7.13 mmol) of sodium methoxide in 25 mL of methanol at a temperature in the region of 22° C. under an argon atmosphere. After stirring at a temperature in the region of 22° C. for 2 hours, the solvent is evaporated off under reduced pressure (2.7 kPa). The residue, placed under an argon atmosphere, is taken up in 25 mL of a tetrahydrofuran/dichloromethane (1/1 by volume) mixture and then 0.418 g (1.43 mmol) of 3-chlorocarbonyl-1-(quinol-8-yl)-1H-pyrrole hydrochloride, dissolved in 5 mL of the same tetrahydrofuran/dichloromethane mixture, is added thereto. After stirring at a temperature in the region of 22° C. for 15 hours, the reaction mixture is concentrated to dryness under reduced pressure (2.7 kPa). The residue is triturated with dichloromethane and filtered off, giving a solid S1. The filtrate is concentrated under reduced pressure (2.7 kPa), resulting in 0.085 g of a foam S2. The solid S1 is suspended in water and filtered. 0.09 g of a solid S3 is thus obtained. The filtrate is extracted with ethyl acetate and the organic phase is dried over magnesium sulphate and evaporated under reduced pressure (2.7 kPa) to give 0.045 g of a residue S4. The fractions S2, S3 and S4 are combined and purified by flash chromatography [eluent: ethyl acetate/methanol (8/2 by volume)]. After concentrating the fractions under reduced pressure, a solid is obtained, which solid is triturated in diisopropyl ether and then filtered off and dried under reduced pressure (2.7 kPa), giving 0.176 g of 3-guanidinocarbonyl-1-(quinol-8-yl)-1H-pyrrole in the form of a cream-coloured solid melting at 155° C. Mass spectrum (EI): m/e 279 (M+·), m/e 221.

b) 3-Chlorocarbonyl-1-(quinol-8-yl)-1H-pyrrole hydrochloride 0.45 mL (5.16 mmol) of oxalyl chloride is added to a solution, cooled to a temperature in the region of 5° C., of 0.45 g (1.64 mmol) of 3-carboxy-1-(quinol-8-yl)-1H-pyrrole hydrochloride in 20 mL of dichloromethane under an argon atmosphere. After stirring at a temperature in the region of 22° C. for 15 hours, the reaction mixture is concentrated to dryness under reduced pressure (2.7 kPa), then it is placed under an argon atmosphere and 20 mL of dichloromethane and 0.45 mL (5.16 mmol) of oxalyl chloride are successively added. After stirring at a temperature in the region of 22° C. for 15 hours, concentrating the reaction medium to dryness under reduced pressure (2.7 kPa) gives 0.418 g of 3-chlorocarbonyl-1-(quinol-8-yl)-1H-pyrrole hydrochloride in the form of a cream-coloured solid which is used directly in the following step.

c) 3-Carboxy-1-(quinol-8-yl)-1H-pyrrole hydrochloride 0.539 (12.63 mmol) of lithium hydroxide monohydrate and 10 mL of water are added to a solution, at a temperature in the region of 22° C., of 0.8 g of a 1/1 (evaluated by NMR) mixture of 3-methoxycarbonyl-1-(quinol-8-yl)-1H-pyrrole and of 8-bromoquinoline in 10 mL of tetrahydrofuran. After stirring at the reflux point of the solvent for 15 hours, the reaction mixture is concentrated to dryness under reduced pressure (2.7 kPa) and the residue is dissolved in water. 12 mL of N hydrochloric acid are then added to the solution. A precipitate appears. After stirring at a temperature in the region of 5° C. for 2 hours, the solid is filtered off and dried on a rack, giving 0.45 g of 3-carboxy-1-(quinol-8-yl)-1H-pyrrole hydrochloride in the form of a white solid. IR spectrum (KBr): 3043, 2613, 1673, 1548, 1508, 1278, 1196, 827, 788 and 751 cm$^{-1}$.

d) 3-Methoxycarbonyl-1-(quinol-8-yl)-1H-pyrrole 20 mL of 1,4-dioxane, 0.32 mL of n-dodecane, 1.5 g (7.21 mmol) of 8-bromoquinoline and 0.77 mL (6.41 mmol) of trans-1,2-cyclohexanediamine are added at a temperature in the region of 22° C. under an argon atmosphere to 0.8 g (6.39 mmol) of 3-methoxycarbonyl-1H-pyrrole, 3 g (14.13 mmol) of potassium orthophosphate and 0.09 g (0.47 mmol) of copper iodide. After stirring at a temperature in the region of 100° C. for 15 hours, the reaction mixture is concentrated to dryness under reduced pressure (2.7 kPa). The residue is diluted with 100 mL of ethyl acetate and the solution obtained is washed with twice 100 mL of water and then with 25 mL of saturated aqueous sodium chloride solution. After separating the phases by settling, the organic phase is dried over anhydrous magnesium sulphate, filtered and concentrated to dryness under reduced pressure (2.7 kPa) to give 2 g of a brown oil which is purified by flash chromatography [eluent: cyclohexane/ethyl acetate (80/20 by volume)]. After concentrating the fractions under reduced pressure, 0.8 g of a 1/1 (evaluated by NMR) mixture of 3-methoxycarbonyl-1-(quinol-8-yl)-1H-pyrrole and of 8-bromoquinoline is obtained, which mixture is used without further purifications in the following step.

Example 8 a) 3-Guanidinocarbonyl-1-(isoquinol-4-yl)-1H-pyrrole

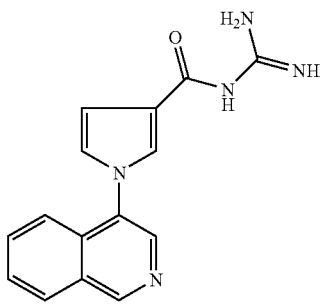

01.46 g (15.28 mmol) of guanidine hydrochloride are added to a solution of 0.83 g (15.36 mmol) of sodium methoxide in 25 mL of methanol at a temperature in the region of 22° C. under an argon atmosphere. After stirring at a temperature in the region of 22° C. for 2 hours, the solvent is evaporated off under reduced pressure (2.7 kPa). The residue, placed under an argon atmosphere, is taken up in 25 mL of a tetrahydrofuran/dichloromethane (1/1 by volume) mixture and then 0.9 g (3.07 mmol) of 3-chlorocarbonyl-1-(isoquinol-4-yl)-1H-pyrrole hydrochloride, dissolved in 5 mL of the same tetrahydrofuran/dichloromethane mixture, is added thereto. After 2 hours at a temperature in the region of 60° C. and then 15 hours at a temperature in the region of 22° C. with stirring, the reaction mixture is concentrated to dryness under reduced pressure (2.7 kPa). The residue is triturated with water and filtered. The solid obtained is discarded. The filtrate is brought to pH 14 by addition of N sodium hydroxide solution and is extracted with dichloromethane (extract E1), then the pH of the aqueous phase is adjusted to pH 6 by addition of N hydrochloric acid and it is again extracted with dichloromethane (extract E2). The organic phases (extracts E1 and E2) are collated, dried over magnesium sulphate and concentrated to dryness. The residue is purified by flash chromatography [eluent: ethyl acetate/methanol (85/25 by volume)]. After concentrating the fractions under reduced pressure, a solid (0.16 g) is obtained, which solid is added to another batch obtained according to an identical protocol (0.18 g). This solid is triturated under hot conditions in diisopropyl ether and then filtered and dried under reduced pressure (2.7 kPa), giving 0.28 g of 3-guanidinocarbonyl-1-(iso-quinol-4-yl)-1H-pyrrole in the form of a cream-coloured solid which decomposes at 209–210° C. Mass spectrum (EI): m/e 279 (M+·), m/e 221. IR spectrum (KBr): 3122, 1701, 1625, 1585, 1508, 1491, 1374, 1308, 1274, 853, 781, 753 and 596 cm$^{-1}$.

b) 3-Chlorocarbonyl-1-(isoquinol-4-yl)-1H-pyrrole hydrochloride 0.82 mL (9.4 mmol) of oxalyl chloride is added to a solution, cooled to a temperature in the region of 5° C., of 0.75 g (3.15 mmol) of 3-carboxy-1-(isoquinol-4-yl)-1H-pyrrole in 25 mL of dichloromethane under an argon atmosphere. After stirring at a temperature in the region of 22° C. for 15 hours, the reaction mixture is concentrated to dryness under reduced pressure (2.7 kPa), resulting in 0.9 g of 3-chlorocarbonyl-1-(isoquinol-4-yl)-1H-pyrrole hydrochloride in the form of a cream-coloured solid which is used directly in the following step.

c) 3-Carboxy-1-(isoquinol-4-yl)-1H-pyrrole 0.63 g (15.02 mmol) of lithium hydroxide monohydrate and 20 mL of water are added to a solution, at a temperature in the region of 22° C., of 0.95 g (376 mmol) of 3-methoxycarbonyl-1-(isoquinol-4-yl)-1H-pyrrole in 20 mL of tetrahydrofuran. After stirring at the reflux point of the solvent for 15 hours, the reaction mixture is concentrated to dryness under reduced pressure (2.7 kPa) and the residue is dissolved in water. The solution is extracted with ethyl acetate and the organic phase is discarded. The aqueous phase is adjusted to pH 6 with N hydrochloric acid and extracted with ethyl acetate. The organic phase is washed successively with water and with saturated aqueous sodium chloride solution and then it is dried over magnesium sulphate and concentrated to dryness under reduced pressure (2.7 kPa), resulting in 0.75 g of 3-carboxy-1-(isoquinol-4-yl)-1H-pyrrole in the form of a beige-coloured solid. IR spectrum (KBr): 3153, 2518, 1855, 1690, 1495, 1276, 1188, 933, 808, 783, 757, 712 and 675 cm$^{-1}$.

d) 3-Methoxycarbonyl-1-(isoquinol-4-yl)-1H-pyrrole 20 mL of 1,4-dioxane, 0.32 mL of n-dodecane, 1.5 g (7.21 mmol) of 4-bromoisoquinoline and 0.77 mL (6.41 mmol) of trans-1,2-cyclohexanediamine are added at a temperature in the region of 22° C. under an argon atmosphere to 0.8 g (6.39 mmol) of 3-methoxycarbonyl-1H-pyrrole, 3 g (14.13 mmol) of potassium orthophosphate and 0.09 g (0.47 mmol) of copper iodide. After stirring at a temperature in the region of 100° C. for 15 hours, the reaction mixture is concentrated to dryness under reduced pressure (2.7 kPa). The residue is diluted with 100 mL of ethyl acetate and the solution obtained is washed with twice 100 mL of water and then with 25 mL of saturated aqueous sodium chloride solution. After separating the phases by settling, the organic phase is dried over anhydrous magnesium sulphate, filtered and concentrated to dryness under reduced pressure (2.7 kPa) to give 2 g of a brown oil which is purified by flash chromatography [eluent: cyclohexane/ethyl acetate (75/25 by volume)]. After concentrating the fractions under reduced pressure, 0.95 g of 3-methoxycarbonyl-1-(isoquinol-4-yl)-1H-pyrrole is obtained in the form of a yellow oil. IR spectrum (CCl4): 2950, 1722, 1547, 1495, 1273, 1196, 1178, 1143, 1003, 927 and 633 cm$^{-1}$.

Example 9 a) 3-Guanidinocarbonyl-4-methyl-1-(quinol-4-yl)-1H-pyrrole

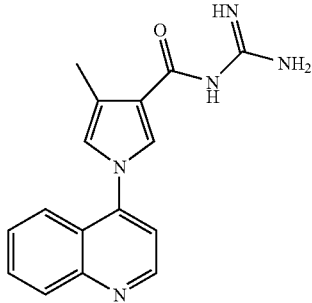

1.4 g (25.5 mmol) of sodium methoxide is added at a temperature in the region of 20° C. under an argon atmosphere to 25 mL of methanol. After complete dissolution, 2.5 g (26.2 mmol) of guanidine hydrochloride are added. After stirring at a temperature in the region of 20° C. for 1 hour, the reaction mixture is concentrated to dryness under reduced pressure (2.7 kPa) to give a residue which is suspended in 25 mL of 1,2-dimethoxyethane and then again concentrated to dryness. The residue is suspended in a mixture of 75 mL of tetrahydrofuran and 50 mL of dichloromethane at a temperature in the region of 20° C. under an argon atmosphere, and then 1.07 g (3.97 mmol) of 3-chlorocarbonyl-4-methyl-1-(quinol-4-yl)-1H-pyrrole, dissolved in 25 mL of chloroform, are added thereto. After stirring at a temperature in the region of 20° C. for 18 hours, the reaction mixture is concentrated to dryness under reduced pressure (2.7 kPa) to give a residue which is triturated in 100 mL of water. After filtering, a gum is obtained, which gum is triturated in 50 mL of methanol and filtered. The filtrate is partially concentrated to a volume of 5 to 10 mL and is then purified by silica gel chromatography [eluent: chloroform/methanol (75/25 by volume)]. After concentrating the fractions under reduced pressure and triturating in ethyl ether, 0.64 g of 3-guanidinocarbonyl-4-methyl-1-(quinol-4-yl)-1H-pyrrole is obtained in the form of an off-white solid melting at 215° C. Mass spectrum (EI): m/e 293 (M$^{+\cdot}$), m/e 234.

b) 3-Chlorocarbonyl-4-methyl-1-(quinol-4-yl)-1H-pyrrole 10 mL (137 mmol) of sulphinyl chloride are added at a temperature in the region of 20° C. under an argon atmosphere to 1 g (3.97 mmol) of 3-carboxy-4-methyl-1-(quinol-4-yl)-1H-pyrrole dissolved in 20 mL of chloroform. After stirring at the reflux point of the solvent for 1 hour, the reaction mixture is concentrated to dryness under reduced pressure (2.7 kPa). The residue is dissolved in 20 mL of chloroform and then brought back to dryness to give 1.07 g (3.97 mmol) of 3-chlorocarbonyl-4-methyl-1-(quinol-4-yl)-1H-pyrrole in the form of a beige-coloured solid which is used directly in the following step.

c) 3-Carboxy-4-methyl-1-(quinol-4-yl)-1H-pyrrole 0.63 g (15 mmol) of lithium hydroxide monohydrate is added at a temperature in the region of 20° C. to 1.21 g (4.54 mmol) of 3-methoxycarbonyl-4-methyl-1-(quinol-4-yl)-1H-pyrrole dissolved in 50 mL of tetrahydrofuran and 50 mL of water. After stirring at reflux for 22 hours, the reaction mixture is concentrated to dryness under reduced pressure (2.7 kPa) to give a residue which is taken up in 20 mL of water and then triturated with 15 mL of 1N hydrochloric acid. After filtering off and drying the solid residue at ambient pressure at a temperature in the region of 50° C., 1.05 g of 3-carboxy-4-methyl-1-(quinol-4-yl)-1H-pyrrole are obtained in the form of a whitish solid. Mass spectrum (EI): EI: m/e 252 (M$^{+\cdot}$) m/e 207.

d) 3-Methoxycarbonyl-4-methyl-1-(quinol-4-yl)-1H-pyrrole 0.208 g (6.5 mmol) of sodium hydride, at 75% by weight in liquid petroleum jelly, is added at a temperature in the region of 20° C. under an argon atmosphere to a solution of 0.903 g (6.5 mmol) of 3 methoxycarbonyl-4-methyl-1H-pyrrole in 20 mL of dimethylformamide. After stirring at a temperature in the region of 40° C. for 0.3 hour, 1.07 g (6.5 mmol) of 4-chloroquinoline and 10 mL of dimethylformamide are added. After stirring at a temperature in the region of 120° C. for 4 hours, the reaction mixture is poured into 200 mL of salt water and then extracted with 100 mL of ethyl acetate. The organic phase is partially concentrated under reduced pressure. 100 mL of salt water are added to the residue, which is then extracted with 50 mL of ethyl acetate. The organic phase is dried over anhydrous magnesium sulphate, filtered and then concentrated to dryness under reduced pressure (2.7 kPa) to give 1.8 g of a solid which is purified by silica gel chromatography [eluent: dichloromethane/ethyl acetate (75/25 by volume)]. After concentrating the fractions under reduced pressure (2.7 kPa), 1.23 g of 3-methoxycarbonyl-4-methyl-1-(quinol-4-yl)-1H-pyrrole are obtained in the form of a white solid. Mass spectrum (EI): m/e 266 (M$^{+\cdot}$), m/e 235.

e) 3-Methoxycarbonyl-4-methyl-1H-pyrrole can be obtained by the method described by A. M. Leusen et al., Tetrahedron Lett., 52, 5337 (1972) which is incorporated by reference herein.

Example 10 a) 3-Guanidinocarbonyl-1-(isoquinol-1-yl)$_4$-methyl-1H-pyrrole hydrochloride

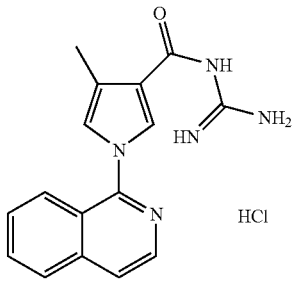

1.37 g (25.37 mmol) of sodium methoxide are added at a temperature in the region of 20° C. under an argon atmosphere to 25 mL of methanol. After complete dissolution, 2.5 g (26.2 mmol) of guanidine hydrochloride are added. After stirring at a temperature in the region of 20° C. for 1 hour, the reaction mixture is concentrated to dryness under reduced pressure (2.7 kPa) to give a residue which is suspended in 25 mL of 1,2-dimethoxyethane and then again concentrated to dryness. The residue is suspended in a mixture of 50 mL of tetrahydrofuran, 25 mL of acetonitrile and 50 mL of dichloromethane at a temperature in the region of 20° C. under an argon atmosphere and then 1.18 g (4.36 mmol) of 3-chlorocarbonyl-1-(isoquinol-1-yl)-4-methyl-1H-pyrrole, dissolved in 20 mL of chloroform, are added thereto. After stirring at a temperature in the region of 20° C. for 18 hours, the reaction mixture is concentrated to dryness under reduced pressure (2.7 kPa) to give a residue which is triturated in 100 mL of water. After filtering, a gum is obtained, which gum is dissolved in 50 mL of methanol. The solution obtained is partially concentrated to a volume of 5 to 10 mL and is then purified by silica gel chromatography [eluent: chloroform/methanol (75/25 by volume)]. After concentrating the fractions under reduced pressure and triturating in ethyl ether, 0.62 g of 3-guanidinocarbonyl-1-(isoquinol-1-yl)-4-methyl-1H-pyrrole hydrochloride is obtained in the form of a white solid melting at 247° C. Mass spectrum (EI): EI: m/e 293 (M+·), m/e 234.

b) 3-Chlorocarbonyl-1-(isoquinol-1-yl)-4-methyl-1H-pyrrole 10 mL (137 mmol) of sulphinyl chloride are added at a temperature in the region of 20° C. under an argon atmosphere to 1.1 g (4.36 mmol) of 3-carboxy-1-(isoquinol-1-yl)-4-methyl-1H-pyrrole dissolved in 20 mL of chloroform. After stirring at the reflux point of the solvent for 2 hours, the reaction mixture is concentrated to dryness under reduced pressure (2.7 kPa). The residue is dissolved in 20 mL of chloroform and is then brought back to dryness to give 1.18 g (4.36 mmol) of 3-chlorocarbonyl-1-(isoquinol-1-yl)-4-methyl-1H-pyrrole in the form of a beige-coloured solid which is used directly in the following step.

c) 3-Carboxy-1-(isoquinol-1-yl)-4-methyl-1H-pyrrole 0.63 g (15 mmol) of lithium hydroxide monohydrate is added at a temperature in the region of 20° C. to 1.35 g (5 mmol) of 1-(isoquinol-1-yl)-3-methoxycarbonyl-4-methyl-1H-pyrrole dissolved in 50 mL of tetrahydrofuran and 50 mL of water. After stirring at reflux for 25 hours, the reaction mixture is concentrated to dryness under reduced pressure (2.7 kPa) to give a residue which is taken up in 20 mL of water and then triturated with 15 mL of 1N hydrochloric acid. After filtering off and drying the solid residue at ambient pressure at a temperature in the region of 50° C., 1.1 g of 3-carboxy-1-(isoquinol-1-yl)-4-methyl-1H-pyrrole are obtained in the form of a whitish solid melting at 245° C.

d) 1-(Isoquinol-1-yl)-3-methoxycarbonyl-4-methyl-1H-pyrrole 0.208 g (6.5 mmol) of sodium hydride, at 75% by weight in liquid petroleum jelly, is added at a temperature in the region of 20° C. under an argon atmosphere to a solution of 0.903 g (6.5 mmol) of 3-methoxycarbonyl-4-methyl-1H-pyrrole in 20 mL of dimethylformamide. After stirring at a temperature in the region of 40° C. for 0.3 hour, 1.07 g (6.5 mmol) of 1-chloroisoquinoline and 10 mL of dimethylformamide are added. After stirring at a temperature in the region of 120° C. for 4 hours, the reaction mixture is poured into 200 mL of salt water and then extracted with 100 mL of ethyl acetate. The organic phase is partially concentrated under reduced pressure. 100 mL of salt water are added to the residue, which is then extracted with 50 mL of ethyl acetate. The organic phase is dried over anhydrous magnesium sulphate, filtered and then concentrated to dryness under reduced pressure (2.7 kPa) to give a solid which is purified by silica gel chromatography [eluent: cyclohexane/dichloromethane/ethyl acetate (60/36/4 by volume)]. After concentrating the fractions under reduced pressure (2.7 kPa), 1.5 g of 1-(isoquinol-1-yl)-3-methoxycarbonyl-4-methyl-1H-pyrrole are obtained. Mass spectrum (EI): m/e 266 (M+·), m/e 235.

e) 3-Methoxycarbonyl-4-methyl-1H-pyrrole can be obtained by the method described by A. M. Leusen et al., Tetrahedron Lett., 52, 5337 (1972), which is incorporated by reference herein.

Example 11 a) 3-Guanidinocarbonyl-4,5-dimethyl-1-(quinol-4-yl)-1H-pyrrole dihydrochloride

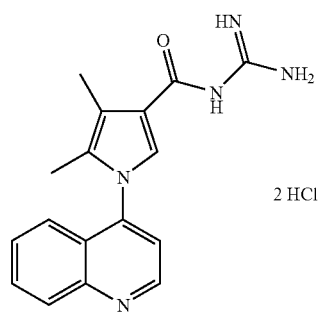

1.78 g (33 mmol) of sodium methoxide are added at a temperature in the region of 20° C. under an argon atmosphere to 20 mL of methanol. After complete dissolution, 3.34 g (35 mmol) of guanidine hydrochloride are added. After stirring at a temperature in the region of 20° C. for 0.5 hour, the reaction mixture is concentrated to dryness under reduced pressure (2.7 kPa) to give a residue which is suspended in 25 mL of 1,2-dimethoxyethane and then again concentrated to dryness. The residue is suspended in a mixture of 75 mL of tetrahydrofuran and 50 mL of dichloromethane at a temperature in the region of 20° C. under an argon atmosphere and then 1.17 g (4.1 mmol) of 3-chlorocarbonyl-4,5-dimethyl-1-(quinol-4-yl)-1H-pyrrole, dissolved in 25 mL of chloroform, are added thereto. After stirring at a temperature in the region of 20° C. for 18 hours, the reaction mixture is concentrated to dryness under reduced pressure (2.7 kPa) to give a residue which is triturated in 100 mL of water. After filtering, a gum is obtained, which gum is triturated in 50 mL of methanol and filtered. The solution obtained is partially concentrated to a volume of 5 to 10 mL and then purified by silica gel chromatography [eluent: chloroform/methanol (90/10 and then 70/30 by volume)]. After concentrating the fractions under reduced pressure, an oil is obtained, which oil is dissolved in ethanol and to which is added 4 mL of a 5.3N solution of hydrochloric acid in dioxane. The solution obtained is concentrated to dryness under reduced pressure (2.7 kPa) to give a residue which is triturated in a mixture of isopropanol and isopropyl acetate. 0.96 g of 3-guanidinocarbonyl-4,5-dimethyl-1-(quinol-4-yl)-1H-pyrrole dihydrochloride is thus obtained in the form of a yellow solid which decomposes at a temperature of greater than 260° C. Mass spectrum (EI): m/e 307 (M+) m/e 248. IR spectrum (KBr): 3371, 3103, 2622, 1694, 1599, 1495, 1423, 1308, 1251, 1194, 1093 and 754 cm$^{-1}$.

b) 3-Chlorocarbonyl-4,5-dimethyl-1-(quinol-4-yl)-1H-pyrrole 10 mL (137 mmol) of sulphinyl chloride are added at a temperature in the region of 20° C. under an argon atmosphere to 1.1 g (4.1 mmol) of 3-carboxy-4,5-dimethyl-1-(quinol-4-yl)-1H-pyrrole dissolved in 20 mL of chloroform. After stirring at the reflux point of the solvent for 1.5 hours, the reaction mixture is concentrated to dryness under reduced pressure (2.7 kPa). The residue is dissolved in 20 mL of chloroform and is then brought back to dryness to give 1.17 g (4.1 mmol) of 3-chlorocarbonyl-4,5-dimethyl-1-(quinol-4-yl)-1H-pyrrole in the form of a brown-yellow solid which is used directly in the following step.

c) 3-Carboxy-4,5-dimethyl-1-(quinol-4-yl)-1H-pyrrole 1.89 g (45 mmol) of lithium hydroxide monohydrate are added at a temperature in the region of 20° C. to 1.3 g (4.42 mmol) of 3-ethoxycarbonyl-4,5-dimethyl-1-(quinol-4-yl)-1H-pyrrole dissolved in 50 mL of tetrahydrofuran and 50 mL of water. After stirring at reflux for 42 hours, the reaction mixture is concentrated virtually to dryness under reduced pressure (2.7 kPa) to give a residue that is taken up in 41 mL of 1N hydrochloric acid. After filtering off and drying the solid residue at ambient pressure at a temperature in the region of 50° C., 1.1 g of 3-carboxy-4,5-dimethyl-1-(quinol-4-yl)-1H-pyrrole are obtained in the form of a whitish solid melting at approximately 238° C.

d) 3-Ethoxycarbonyl-4,5-dimethyl-1-(quinol-4-yl)-1H-pyrrole 0.285 g (8.9 mmol) of sodium hydride, at 75% by weight in liquid petroleum jelly, is added at a temperature in the region of 20° C. under an argon atmosphere to a solution of 1.35 g (8.1 mmol) of 3-ethoxycarbonyl-4,5-dimethyl-1H-pyrrole in 8 mL of dimethylformamide. After stirring at a temperature in the region of 40° C. for 0.3 hour, 1.45 g (8.9 mmol) of 4-chloroquinoline and 2 mL of dimethylformamide are added. After stirring at a temperature in the region of 140° C. for 6 hours, the reaction mixture is poured into 100 mL of salt water and then extracted with twice 50 mL of ethyl acetate. The combined organic phases are washed with 15 mL of water, carefully separated by settling and then concentrated to dryness under reduced pressure (2.7 kPa) to give a brown oil which is purified by silica gel chromatography [eluent: cyclohexane/ethyl acetate (75/25 by volume)]. After concentrating the fractions under reduced pressure (2.7 kPa), 1.32 g of 3-ethoxycarbonyl-4,5-dimethyl-1-(quinol-4-yl)-1H-pyrrole are obtained in the form of a yellowish oil. $^1$H NMR spectrum (300 MHz, d6-(CD$_3$)$_2$SO, δ in ppm): 1.27 (t, J=7 Hz, 3H), 1.87 (s, 3H), 2.27 (s, 3H), 4.21 (mt, 2H), 7.37 (dd, J=8 and 1 Hz, 1H), 7.55 (s, 1H), 7.62 (d, J=5 Hz, 1H), 7.70 (ddd, J=8, 7 and 1 Hz, 1H), 7.89 (ddd, J=8, 7 and 1 Hz, 1H), 8.19 (broad d, J=8 Hz, 1H), 9.07 (d, J=5 Hz, 1H).

e) 3-Ethoxycarbonyl-4,5-dimethyl-1H-pyrrole can be obtained by the method described by F. Korte et al., Chem. Ber., 95, 307–318 (1962), which is incorporated by reference herein.

Example 12 a) 4-Cyclopropyl-3-guanidinocarbonyl-1-(quinolin-4-yl)-1H-pyrrole dihydrochloride

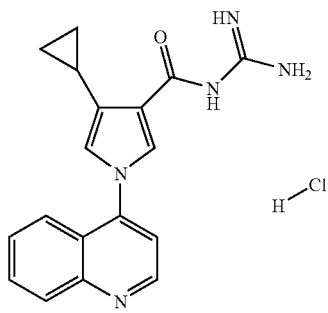

1.19 g (22 mmol) of sodium methoxide are added to 25 mL of methanol at a temperature in the region of 20° C. under an argon atmosphere. After total dissolution, 2.2 g (23 mmol) of guanidine hydrochloride are added. After stirring at a temperature in the region of 20° C. for 0.5 hour, the reaction mixture is concentrated to dryness under reduced pressure (2.7 kPa) to give a residue, which is suspended in 50 mL of 1,2-dimethoxyethane and then concentrated to dryness again. The residue is suspended in a mixture of 100 mL of tetrahydrofuran and 100 mL of dichloromethane at a temperature in the region of 20° C. under an argon atmosphere, and 1.12 g (3.78 mmol) of 3-chlorocarbonyl-4-cyclopropyl-1-(quinolin-4-yl)-1H-pyrrole dissolved in 25 mL of chloroform are then added. After stirring for 17 hours at a temperature in the region of 20° C., the reaction mixture is concentrated to dryness under reduced pressure (2.7 kPa) to give a residue, which is triturated in 100 mL of water. After filtration, a gum is obtained, which is dissolved in 50 mL of methanol. The solution is partially concentrated to a volume of from 5 to 10 mL and then purified by chromatography on silica gel [eluent: chloroform/methanol (75/25 by volume)]. After the fractions containing the expected product have been concentrated to dryness under reduced pressure, the residue is dissolved in 20 mL of methanol, and 2 mL of 6 N hydrochloric dioxane are added. The solution obtained is concentrated to dryness under reduced pressure (2.7 kPa) and the residue is then triturated in a mixture of dichloromethane and diethyl ether and filtered, giving 0.77 g of 4-cyclopropyl-3-guanidinocarbonyl-1-(quinolin-4-yl)-1H-pyrrole in the form of a yellow solid melting at 185° C. Mass spectrum (EI): m/e 319 (M$^{+•}$) (base peak), m/e 260, m/e 231.

b) 3-Chlorocarbonyl-4-cyclopropyl-1-(quinolin-4-yl)-1H-pyrrole 10 mL (137 mmol) of sulphinyl chloride are added to 1.05 g (3.78 mmol) of 3-carboxy-4-cyclopropyl-1-(quinolin-4-yl)-1H-pyrrole dissolved in 20 mL of chloroform at a temperature in the region of 20° C. under an argon atmosphere. After stirring for one hour at the reflux temperature of the solvent, the reaction mixture is concentrated to dryness under reduced pressure (2.7 kPa). The residue is dissolved in 20 mL of chloroform and then concentrated to dryness again, giving 1.12 g (3.78 mmol) of 3-chlorocarbonyl-4-cyclopropyl-1-(quinolin-4-yl)-1H-pyrrole in the form of a yellow solid, which is used directly in the following step.

c) 3-Carboxy-4-cyclopropyl-1-(quinolin-4-yl)-1H-pyrrole 0.63 g (15 mmol) of lithium hydroxide monohydrate is added, at a temperature in the region of 20° C., to 1.3 g (4.4 mmol) of 4-cyclopropyl-3-methoxycarbonyl-1-(quinolin-4-yl)-1H-pyrrole dissolved in 50 mL of tetrahydrofuran and 50 mL of water. After stirring for 26 hours at the reflux temperature of the solvent, the reaction mixture is concentrated to dryness under reduced pressure (2.7 kPa). The residue is taken up in 20 mL of water and then triturated with 15 mL of 1 N hydrochloric acid. After the solid residue has been filtered off and dried at a temperature in the region of 50° C. at atmospheric pressure, 1.05 g of 3-carboxy-4-cyclopropyl-1-(quinolin-4-yl)-1H-pyrrole are obtained in the form of a cream-colored solid melting at 195° C.

d) 4-Cyclopropyl-3-methoxycarbonyl-1-(quinolin-4-yl)-1H-pyrrole 0.208 g (6.5 mmol) of sodium hydride at 75% by weight in liquid petroleum jelly is added to a solution of 1.07 g (6.5 mmol) of 4-cyclopropyl-3-methoxycarbonyl-1H-pyrrole in 20 mL of dimethylformamide at a temperature in the region of 20° C. under an argon atmosphere. After the reaction mixture has been stirred at a temperature in the region of 40° C. for 0.3 hour, 1.07 g (6.5 mmol) of 4-chloroquinoline and 10 mL of dimethylformamide are added. After stirring for 6 hours at a temperature in the region of 120° C., the reaction mixture is poured into 200 mL of brine and then extracted with 100 mL and then 50 mL of ethyl acetate. The organic extracts are combined and then concentrated to dryness under reduced pressure (2.7 kPa). The oily residue is purified by chromatography on silica gel [eluent: dichloromethane/ethyl acetate (75/25 by volume)]. After the fractions containing the expected product have been concentrated to dryness under reduced pressure (2.7 kPa), 1.2 g of 4-cyclopropyl-3-methoxycarbonyl-1-(quinolin-4-yl)-1H-pyrrole are obtained in the form of a thick clear oil, which is used directly in the following step.

e) 4-Cyclopropyl-3-methoxycarbonyl-1H-pyrrole

A solution of 8.77 g of p-toluenesulphonylmethyl isocyanide and 5.67 g of methyl 3-cyclopropylacrylate in 72 mL of dimethyl sulphoxide and 145 mL of diethyl ether is added dropwise over 1.5 hours and under an argon atmosphere to a suspension of 1.73 g (54 mmol) of sodium hydride (at 75% by weight in liquid petroleum jelly) in 90 mL of diethyl ether. The reaction is exothermic. After the reaction mixture has been stirred at room temperature for 2.75 hours, 180 mL of brine are added cautiously, and the mixture is extracted twice with 100 mL of diethyl ether. The organic phase is washed with water, dried and then concentrated to dryness under reduced pressure (2.7 kPa), giving 6.39 g of 4-cyclopropyl-3-methoxycarbonyl-1H-pyrrole in the form of a yellow solid melting at 107° C.

f) Methyl 3-cyclopropylacrylate can be obtained by the method described by L. Blackburn et al., Chem. Commun., 1999, 1337–1338, which is incorporated by reference herein.

Example 13 a) 3-Guanidinocarbonyl-4-methyl-1-(quinolin-5-yl)-1H-pyrrole hydrochloride

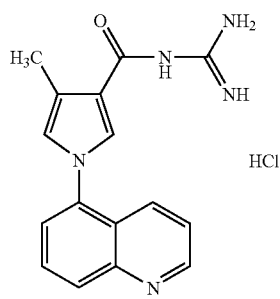

1.06 g (11.18 mmol) of guanidine hydrochloride is added to a solution of 0.604 g (11.18 mmol) of sodium methoxide in 50 mL of methanol at a temperature in the region of 20° C. under an argon atmosphere. After stirring for 2 hours at this temperature, the mixture is concentrated to dryness under reduced pressure (2.7 kPa). The residue is taken up in 25 mL of 1,2-dimethoxyethane, and 0.57 g (1.86 mmol) of 3-chlorocarbonyl-4-methyl-1-(quinolin-5-yl)-1H-pyrrole hydrochloride is added. After stirring for 2 hours at a temperature in the region of 20° C., the reaction mixture is concentrated to dryness under reduced pressure (2.7 kPa). The residue is triturated in 25 mL of water and then filtered, giving a gum, which is triturated again in 20 mL of water and filtered. The residue is purified by chromatography on silica gel [eluent: chloroform/methanol (80/20 by volume)]. After the fractions containing the expected product have been concentrated to dryness under reduced pressure, the residue is dissolved in ethyl acetate, and excess 4 M hydrochloric ether is added. After the reaction mixture has been stirred at room temperature for one hour, the precipitate formed is isolated by filtration, giving 0.25 g of 3-guanidinocarbonyl-4-methyl-1-(quinolin-5-yl)-1H-pyrrole hydrochloride in the form of a yellow solid melting at 240° C. Mass spectrum (EI): m/e 293 (M$^+$·) (base peak).

b) 3-Chlorocarbonyl-4-methyl-1-(quinolin-5-yl)-1H-pyrrole hydrochloride 8 mL (110 mmol) of sulphinyl chloride are added to 0.47 g (1.86 mmol) of 3-carboxy-4-methyl-1-(quinolin-5-yl)-1H- pyrrole dissolved in 25 mL of chloroform at a temperature in the region of 20° C. under an argon atmosphere. After stirring for 1.5 hours at the reflux temperature of the solvent, the reaction mixture is concentrated to dryness under reduced pressure (2.7 kPa). The residue is dissolved in 25 mL of chloroform and then concentrated to dryness again, giving 0.58 g (1.86 mmol) of 3-chlorocarbonyl-4-methyl-1-(quinolin-5-yl)-1H-pyrrole hydrochloride in the form of a beige-colored solid, which is used directly in the following step.

c) 3-Carboxy-4-methyl-1-(quinolin-5-yl)-1H-pyrrole 0.504 g (12.2 mmol) of lithium hydroxide monohydrate is added to 0.8 g (3.04 mmol) of 3-methoxycarbonyl-4-methyl-1-(quinolin-5-yl)-1H-pyrrole dissolved in 25 mL of tetrahydrofuran and 25 mL of water at a temperature in the region of 20° C. After stirring for 30 hours at the reflux temperature of the solvent, the reaction mixture is concentrated to dryness under reduced pressure (2.7 kPa). The residue is taken up in 20 mL of water and then neutralized with 1 N hydrochloric acid. The mixture is filtered, and the solid residue obtained is dried, giving 0.5 g of 3-carboxy-4-methyl-1-(quinolin-5-yl)-1H-pyrrole in the form of a cream-colored solid, melting above 260° C., which is used directly in the following step.

d) 3-Methoxycarbonyl-4-methyl-1-(quinolin-5-yl)-1H-pyrrole 12 mL of 1,4-dioxane, 0.27 mL of n-dodecane, 2.3 g (9.017 mmol) of 5-iodoquinoline and 0.863 mL (7.19 mmol) of trans-1,2-cyclohexanediamine are added to 1 g (7.18 mmol) of 3-methoxycarbonyl-4-methyl-1H-pyrrole, 3.2 g (15.09 mmol) of potassium orthophosphate and 0.1 g (0.47 mmol) of copper iodide at a temperature in the region of 22° C. under an argon atmosphere. After stirring for 24 hours at a temperature in the region of 110° C., the reaction mixture is concentrated to dryness under reduced pressure (2.7 kPa). The residue is diluted with 300 mL of ethyl acetate, and the solution obtained is washed three times with 100 mL of water and then with 100 mL of saturated aqueous sodium chloride solution. After separation of the phases by settling, the organic phase is dried over anhydrous magnesium sulphate, filtered and concentrated to dryness under reduced pressure (2.7 kPa), giving 2.5 g of a yellow oil, which is purified by flash chromatography on silica gel [eluent: cyclohexane/ethyl acetate (80/20 by volume)]. After the fractions containing the expected product have been concentrated to dryness under reduced pressure, 0.85 g of 3-methoxycarbonyl-4-methyl-1-(quinolin-5-yl)-1H-pyrrole is obtained in the form of an amber-colored solid melting at 73° C.

e) 3-Methoxycarbonyl-4-methyl-1H-pyrrole can be obtained by the method described by A. M. Leusen et al., Tetrahedron Lett., 52, 5337 (1972). The 5-iodoquinoline can be prepared according to the method described by M. Istrati, C. R. Hebd. Seances Acad. Sci. (1898), 127, 521, which is incorporated by reference herein.

Example 14 a) 4-Trifluoromethyl-3-guanidinocarbonyl-1-(quinolin-4-yl)-1H-pyrrole

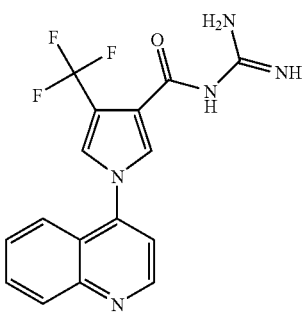

0.841 g (7.5 mmol) of potassium tert-butoxide is added to 0.86 g (9 mmol) of guanidine hydrochloride dissolved in 20 mL of dimethylformamide at a temperature in the region of 20° C. under an argon atmosphere. After the reaction mixture has been stirred at a temperature in the region of 20° C. for 1 hour, 0.501 g (1.5 mmol) of 3-ethoxycarbonyl-4-trifluoromethyl-1-(quinolin-4-yl)-1H-pyrrole is added. After stirring for 65 hours at a temperature in the region of 60° C., the reaction mixture is cooled and then concentrated to dryness under reduced pressure (2.7 kPa), giving 1.9 g of a yellow oil, which is purified by flash chromatography on silica gel [eluent: dichloromethane/methanol/acetonitrile (90/5I5 by volume) and then chloroform/methanol/28% aqueous ammonia (120/30/2.5 by volume)]. After the fractions containing the expected product have been concentrated to dryness under reduced pressure, 0.21 g of 4-trifluoromethyl-3-guanidinocarbonyl-1-(quinolin-4-yl)-1H-pyrrole is obtained in the form of a white foam. IR spectrum (KBr): 3412; 1595; 1556; 1539; 1511; 1349; 1323; 1123; 1034; 870; 812 and 766 cm$^{-1}$. Mass spectrum (EI): m/e 347 (M$^{+\cdot}$), m/e 289.

b) 3-Ethoxycarbonyl-4-trifluoromethyl-1-(quinolin-4-yl)-1H-pyrrole 1.73 g (12.5 mmol) of potassium carbonate are added to 1.036 g (5 mmol) of 3-ethoxycarbonyl-4-trifluoromethyl-1H-pyrrole and 0.82 g (5 mmol) of 4-chloroquinoline dissolved in 10 mL of dimethyl sulphoxide at a temperature in the region of 20° C. under an argon atmosphere. After stirring for 18 hours at a temperature in the region of 110° C., the reaction mixture is poured into 30 mL of water and then left to crystallize for 1 hour at 20° C. After the solid residue has been filtered off and air-dried, 1.48 g of 3-ethoxycarbonyl-4-trifluoromethyl-1-(quinolin-4-yl)-1H-pyrrole are obtained in the form of beige-colored crystals melting at 108° C. IR spectrum (KBr): 3139; 1718; 1564; 1537; 1511; 1306; 1281; 1249; 1169; 1146; 1123; 1036; 846 and 773 cm$^{1}$.

c) 3-Ethoxycarbonyl-4-trifluoromethyl-1H-pyrrole can be prepared as described by Leusen, A. M. et al., Tetrahedron Lett. (1972), (52), 5337–5340, which is incorporated by reference herein.

Example 15 a) 4-Trifluoromethyl-3-guanidinocarbonyl-1-(isoquinolin-1-yl)-1H-pyrrole hydrochloride

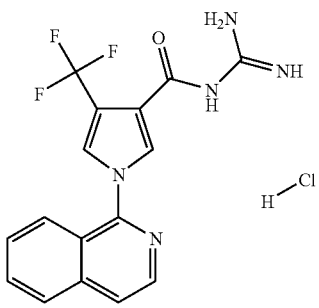

0.388 g (16.89 mmol) of sodium is added to 40 mL of methanol at a temperature in the region of 20° C. under an argon atmosphere. After total dissolution, 1.61 g (16.89 mmol) of guanidine hydrochloride are added. After stirring for 0.5 hour at a temperature in the region of 20° C., the reaction mixture is filtered under an argon atmosphere. The filtrate is concentrated to dryness under reduced pressure (2.7 kPa), giving a residue, which is dissolved in 70 mL of tetrahydrofuran. 1.22 g (3.38 mmol) of 3-chlorocarbonyl-4-trifluoromethyl-1-(isoquinolin-1-yl)-1H-pyrrole hydrochloride dissolved in 30 mL of tetrahydrofuran are then added at a temperature in the region of 20° C. under an argon atmosphere. After stirring for 16 hours at a temperature in the region of 20° C., the reaction mixture is concentrated to dryness under reduced pressure (2.7 kPa). The residue is triturated in 13 mL of water for 17 hours and then filtered and dried under reduced pressure (2.7 kPa) at a temperature in the region of 40° C. The residue is purified by flash chromatography on silica gel [eluent: dichloromethane/methanol/20% aqueous ammonia (120/10/1 by volume)]. After the fractions containing the expected product have been concentrated to dryness under reduced pressure, 0.57 g of a white solid is obtained, which is triturated in 10 mL of 1N hydrochloric acid. After filtering off and oven-drying under reduced pressure (2.7 kPa), 0.52 g of 4-trifluoromethyl-3-guanidinocarbonyl-1-(isoquinolin-1-yl)-1H-pyrrole hydrochloride is obtained in the form of white crystals melting at 260° C. IR spectrum (KBr), 3340; 3245; 3169; 3101; 1713; 1698; 1616; 1576; 1560; 1533; 1500; 1400; 1342; 1293; 1271; 1210; 1176; 1145; 1133; 1111; 1046; 1038; 871 and 752 cm$^{-1}$.

b) 3-Chlorocarbonyl-4-trifluoromethyl-1-(isoquinolin-1-yl)-1H-pyrrole hydrochloride 0.62 mL (7.18 mmol) of oxalyl chloride is added to 1.1 g (3.59 mmol) of 3-carboxy-4-trifluoromethyl-1-(isoquinolin-1-yl)-1H-pyrrole dissolved in 30 mL of dichloromethane at a temperature in the region of 20° C. under an argon atmosphere. After stirring for 2 hours at a temperature in the region of 20° C., the reaction mixture is concentrated to dryness under reduced pressure (2.7 kPa), giving 1.22 g of 3-chlorocarbonyl-4-trifluoromethyl-1-(isoquinolin-1-yl)-1H-pyrrole hydrochloride in the form of a cream-colored solid, which is used directly in the following step.

c) 3-Carboxy-4-trifluoromethyl-1-(isoquinolin-2-yl)-1H-pyrrole 1.76 g (41.88 mmol) of lithium hydroxide monohydrate are added in portions of 0.44 g every 18 hours to 1.4 g (4.19 mmol) of 3-ethoxycarbonyl-4-trifluoromethyl-1-(isoquinolin-1-yl)-1H-pyrrole dissolved in 35 mL of tetrahydrofuran and 35 mL of water at a temperature in the region of 20° C. After stirring for 72 hours at the reflux temperature of the solvent, the reaction mixture is concentrated to dryness under reduced pressure (2.7 kPa). The residue is dissolved in 20 mL of water, and the solution is acidified with 3.4 mL of 12N hydrochloric acid. After the solid residue has been filtered off, washed and dried under reduced pressure (2.7 kPa) at a temperature in the region of 40° C., 1.2 g of 3-carboxy-4-trifluoromethyl-1-(isoquinolin-1-yl)-1H-pyrrole are obtained in the form of cream-colored crystals melting at 234° C. IR spectrum (KBr), 3158; 3079; 2966; 2652; 2544; 1725; 1696; 1628; 1568; 1535; 1501; 1409; 1339; 1317; 1287; 1275; 1243; 1219; 1174; 1155; 1148; 1113; 1022; 828; 808; 765; 731; 684 and 677 cm$^{-1}$.

d) 3-Ethoxycarbonyl4-trifluoromethyl-1-(isoquinolin-1-yl)-1H-pyrrole 1.04 g (5 mmol) of 3-ethoxycarbonyl-4-trifluoromethyl-1H-pyrrole and 0.818 g (5 mmol) of 1-chloroisoquinoline are added to 1.73 g (12.5 mmol) of potassium carbonate suspended in 10 mL of dimethyl sulphoxide at a temperature in the region of 20° C. under an argon atmosphere. After stirring for 17 hours at a temperature in the region of 110° C., the reaction mixture is cooled and then diluted with 30 mL of water. The solid formed is filtered off and washed with water and then oven-dried under reduced pressure (2.7 kPa), giving 1.46 g of 3-ethoxycarbonyl-4-trifluoromethyl-1-(isoquinolin-1-yl)-1H-pyrrole in the form of cream-colored crystals. IR spectrum (KBr), 3159; 2983; 2937; 1721; 1628; 1555; 1534; 1502; 1405; 1343; 1290; 1272; 1215; 1179; 1151; 1135; 1120; 1035; 831; 809; 755; 679 and 674 cm$^{-1}$. Mass spectrum (EI) m/e 334 (M$^{+}$), m/e 289.

e) 3-Ethoxycarbonyl-4-trifluoromethyl-1H-pyrrole can be prepared as described by Leusen, A. M. et al., Tetrahedron Lett. (1972), (52), 5337–5340, which is incorporated by reference herein.

Example 16 a) N-[4-Methyl-1-(2-methyl-quinolin-4-yl)-1H-pyrrole-3-carbonyl]-guanidine trifluoroacetate

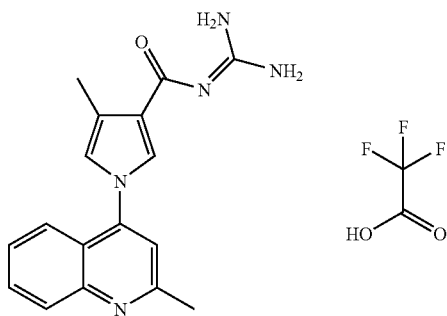

A solution of guanidine is prepared by stirring 5 mmol (560 mg) potassium t-butoxide and 5.5 mmol (525 mg) guanidine hydrochloride in 5 mL dry DMF for 30 minutes at room temperature under exclusion of moisture. To the resulting suspension is added the methyl ester obtained below, the mixture is stirred for 18 h at room temperature under argon. The mixture is filtered and the filtrate directly subjected to purification by prep. HPLC to yield N-[4-methyl-1-(2-methyl-quinolin-4-yl)-1H-pyrrole-3-carbonyl]-guanidine trifluoroacetate as a foam.

The product was characterized by analytical HPLC/MS (Waters 1525 HPLC with Micromass MUX-LCT MS detector; column Merck-Purospher 55*2 mm, 3μ RP18; column temperature: RT; gradient (H2O+0.1% formic acid):(acetonitrile+0.1% formic acid) from 95:5 (0 min) to 5:95 (5 min) to 5:95 (7 min)).

Retention time: 1.72 min, MS molpeak 308 (M+H, electrospray ionisation)

b) 4-Methyl-1-(2-methyl-quinolin-4-yl)-1H-pyrrole-3-carboxylic acid methyl ester 1 mmol (139 mg) of 4-methylpyrrole-3-carboxylic acid methyl ester, 1.1 mmol (195 mg) 4-chloro-2-methyl-quinoline and 1.2 mmol (390 mg) of Cs2CO3 are suspended in 3 mL of dry DMF. The mixture is stirred for 60 h at 80° C. under Argon, allowed to cool to room temperature, and diluted with water (20 mL). Part of the product precipitates and is filtered off. The filtrate is extracted twice with ethyl acetate (20 mL portions). The combined extracts are dried over anhydrous Na$_2$SO$_4$ and evaporated. The residue is combined with the precipitate and purified by prep. HPLC to yield 4-methyl-1-(2-methyl-quinolin-4-yl)-1H-pyrrole-3-carboxylic acid methyl ester (MS molpeak 281 (M$^+$) H, electrospray ionisation)) as an off-white foam after freeze-drying.

The following compounds are prepared in analogy to example 16:

| | | |
|---|---|---|
| 17 | 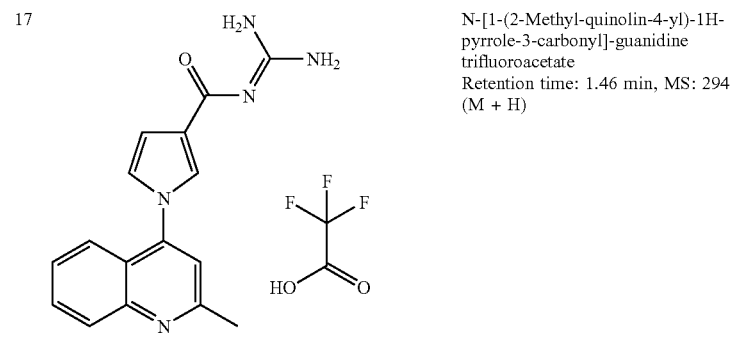 | N-[1-(2-Methyl-quinolin-4-yl)-1H-pyrrole-3-carbonyl]-guanidine trifluoroacetate<br>Retention time: 1.46 min, MS: 294 (M + H) |
| 18 | 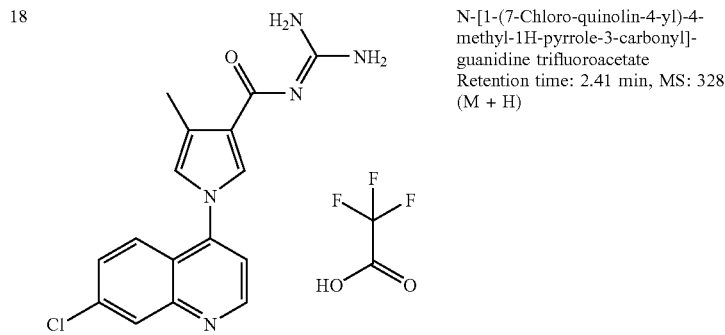 | N-[1-(7-Chloro-quinolin-4-yl)-4-methyl-1H-pyrrole-3-carbonyl]-guanidine trifluoroacetate<br>Retention time: 2.41 min, MS: 328 (M + H) |

-continued

| | | |
|---|---|---|
| 19 | 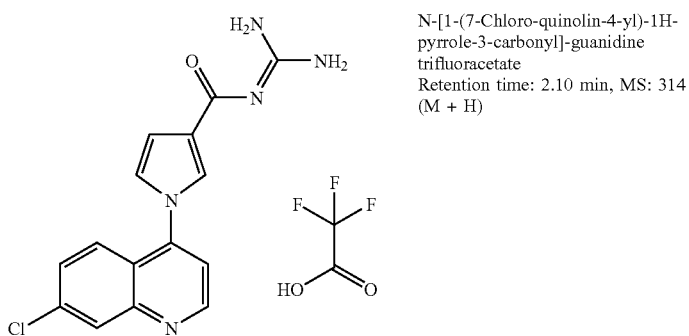 | N-[1-(7-Chloro-quinolin-4-yl)-1H-pyrrole-3-carbonyl]-guanidine trifluoracetate<br>Retention time: 2.10 min, MS: 314 (M + H) |
| 20 | 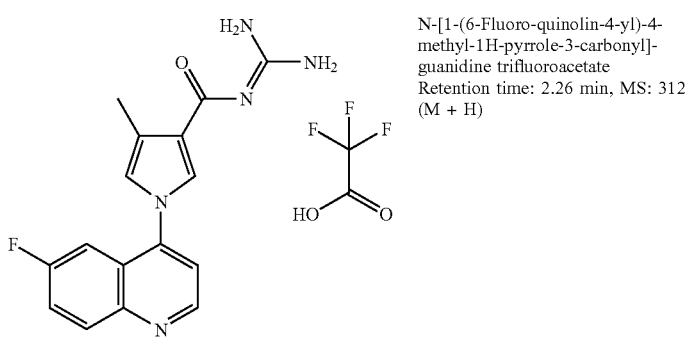 | N-[1-(6-Fluoro-quinolin-4-yl)-4-methyl-1H-pyrrole-3-carbonyl]-guanidine trifluoroacetate<br>Retention time: 2.26 min, MS: 312 (M + H) |
| 21 | 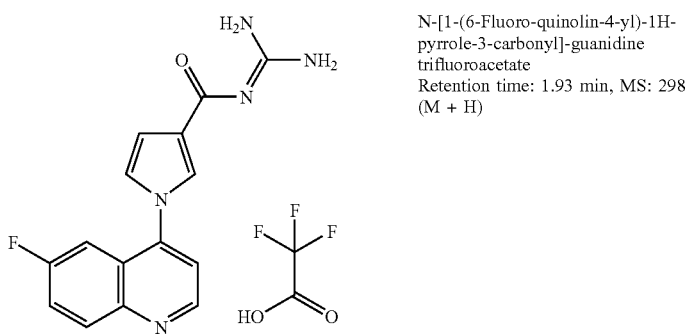 | N-[1-(6-Fluoro-quinolin-4-yl)-1H-pyrrole-3-carbonyl]-guanidine trifluoroacetate<br>Retention time: 1.93 min, MS: 298 (M + H) |
| 22 | 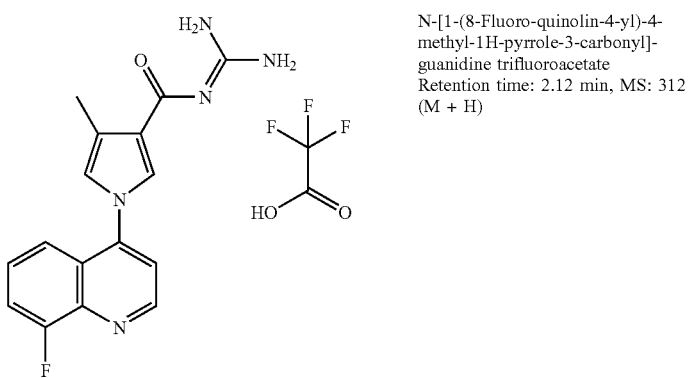 | N-[1-(8-Fluoro-quinolin-4-yl)-4-methyl-1H-pyrrole-3-carbonyl]-guanidine trifluoroacetate<br>Retention time: 2.12 min, MS: 312 (M + H) |

-continued

| | | |
|---|---|---|
| 23 | 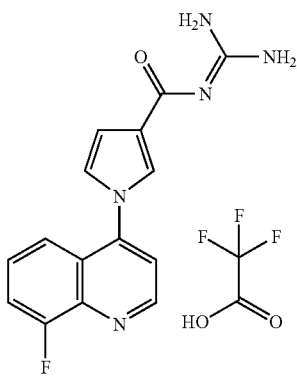 | N-[1-(8-Fluoro-quinolin-4-yl)-1H-pyrrole-3-carbonyl]-guanidine trifluoroacetate<br>Retention time: 1.88 min, MS: 298 (M + H) |
| 24 | 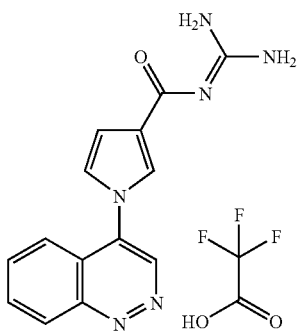 | N-(1-Cinnolin-4-yl-1H-pyrrole-3-carbonyl)-guanidine trifluoroacetate<br>Retention time: 1.66 min, MS: 281 (M + H) |

Example 25 a) N-(4-Methyl-1-pyrimidin-2-yl-1H-pyrrole-3-carbonyl)-guanidine

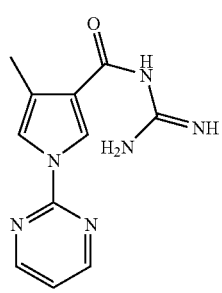

250 mg 4-methyl-1-pyrimidin-2-yl-1H-pyrrole-3-carboxylic acid methyl ester was dissolved in 0.3 mL of NMP. After addition of 1 g guanidine (preparation according to known literature) the mixture was heated under argon for 1 h to 90° C. Completion of the reaction was checked by LCMS. The mixture was cooled to room temperature and then diluted with water, followed by extraction with ethyl acetate. The organic layer was washed with water (twice), dried over anhydrous sodium sulfate. After filtration the solvent was distilled off under reduced pressure and the resulting residue was purified by a silica gel column flash chromatography (eluent: dichloromethane/methanol=5/1) to obtain 150 mg of N-(4-methyl-1-pyrimidin-2-yl-1H-pyrrole-3-carbonyl)-guanidine.

M.p. 208.5° C.

$IC_{50}$=29 nM b) 4-Methyl-1-pyrimidin-2-yl-1H-pyrrole-3-carboxylic acid methyl ester 333.9 mg (2.4 mmol) 4-methyl-1H-pyrrole-3-carboxylic acid methyl ester, 891.5 mg (4.2 mmol) tri-potassium phosphate, 4 mg (0.02 mmol) CuI, 22 mg (0.2 mmol) 1,2-diaminocyclohexane and 317.9 mg (2 mmol) of 2-bromopyrimidine was suspended in 3 mL of dioxane. After addition of 90 μl of dodecane the mixture was heated in a sealed tube under argon for 12 h at 100° C. The mixture was cooled to room temperature and then diluted with water, followed by extraction with ethyl acetate. The organic layer was washed with water (twice), dried over anhydrous sodium sulfate. After filtration the solvent was distilled off under reduced pressure and the resulting residue was purified by a silica gel column flash chromatography (eluent: heptane/dichloromethane/methanol=25/2/1) to obtain 300 mg of 4-Methyl-1-pyrimidin-2-yl-1H-pyrrole-3-carboxylic acid methyl ester as a white solid.

M.p. 107.7° C.

The following compounds were synthesized according to the process described above.

| 26 |  | N-(4-Methyl-1-pyridin-2-yl-1H-pyrrole-3-carbonyl)-guanidine<br>M.p. 217.3° C. |
| --- | --- | --- |
| 27 |  | N-(4-Methyl-1-pyridin-3-yl-1H-pyrrole-3-carbonyl)-guanidine<br>M.p. 230.1° C. |
| 28 |  | N-(4-Methyl-1-pyrimidin-5-yl-1H-pyrrole-3-carbonyl)-guanidine<br>M.p. 241° C. (decomp.) |
| 29 | 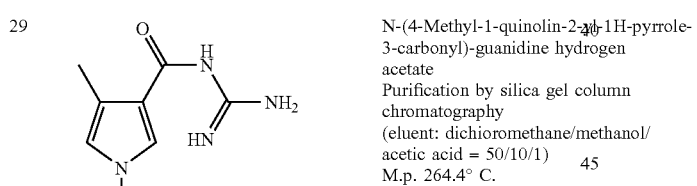 | N-(4-Methyl-1-quinolin-2-yl-1H-pyrrole-3-carbonyl)-guanidine hydrogen acetate<br>Purification by silica gel column chromatography<br>(eluent: dichloromethane/methanol/acetic acid = 50/10/1)<br>M.p. 264.4° C. |
| 30 | 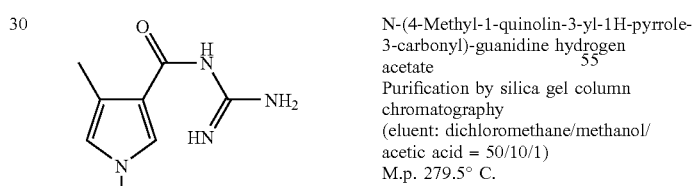 | N-(4-Methyl-1-quinolin-3-yl-1H-pyrrole-3-carbonyl)-guanidine hydrogen acetate<br>Purification by silica gel column chromatography<br>(eluent: dichloromethane/methanol/acetic acid = 50/10/1)<br>M.p. 279.5° C. |

NHE Inhibition Methode

The NHE inhibitory activities ($IC_{50}$ values) of the compounds according to the invention were determined by a FLIPR test.

The test is performed in the FLIPR (Fluorescent Imaging Plate Reader) equipped with clear-bottomed and black-walled 96-well microtitration plates. The transfected cell lines expressing the various NHE subtypes (the parental cell line LAP-1 shows no endogenous NHE activity as a result of mutagenesis and subsequent selection) are seeded the preceding day at a density of ~25000 cells/well.

The growth medium for the transfected cells (Iscove +10% foetal calf serum) also comprises G418 as selection antibiotic to ensure the presence of transfected sequences.

The actual test begins by eliminating the growth medium and adding 100 µl of loading buffer per well (5 µM of BCECF-AM [2',7'-bis(2-carboxyethyl)-5-(6)-carboxyfluoresceine acetoxymethyl ester] in 20 mM of $NH_4Cl$, 115 mM of choline chloride, 1 mM of $CaCl_2$, 5 mM of KCl, 20 mM of HEPES and 5 mM of glucose; pH 7.4 (adjusted with KOH). The cells are then incubated for 20 minutes at 37° C. This incubation results in the loading of the fluorescent dye into the cells, the fluorescence intensity of which depends on the pHi, and on the $NH_4Cl$, which results in a slight basification of the cells.

The precursor BCECF-AM, a non-fluorescent dye, is, as an ester, capable of crossing the membrane. The actual dye, which is incapable of crossing the membrane, is released inside the cell by esterases.

After this 20-minute incubation, the loading buffer, which comprises $NH_4Cl$ and free BCECF-AM, is removed by washing three times in the cell washing device (Tecan Columbus), each wash being performed with 400 µL of washing buffer (133.8 mM of choline chloride, 4.7 mM of KCl, 1.25 mM of $MgCl_2$, 1.25 mM of $CaCl_2$, 0.97 mM of $K_2HPO_4$, 0.23 mM of $KH_2PO_4$, 5 mM of HEPES and 5 mM of glucose; pH 7.4 (adjusted with KOH)). The residual volume remaining in the wells is 90 µL (possibly between 50 and 125 µL). This washing step removes the free BCECF-AM and results in an intracellular acidification (pHi of 6.3–6.4) due to the removal of the external ammonium ions.

As the equilibrium of the intracellular ammonium with the aqueous ammonia and the protons, by removal of the extracellular ammonium and by the subsequent immediate crossing of the aqueous ammonia across the cell membrane, is disrupted, the washing process results in intracellular protons remaining, which is the cause of the intracellular acidification. This acidification can result finally in the death of the cells if it lasts long enough. It is important here for the washing buffer to be free of sodium (<1 mM), otherwise the extracellular sodium ions would result in an immediate increase in the pHi on account of the activity of the cloned NHE isoforms. It is also important for all the buffers used (loading buffer, washing buffer and regeneration buffer) not to contain any $HCO_3$-ions, otherwise the presence of bicarbonate would result in the activation of bicarbonate-dependent systems that disrupt the pHi regulation, which systems are contained in the LAP-1 parental cell line.

The microtiter plates containing acidified cells are then transferred (up to 20 minutes after the acidification) to the FLIPR. In the FLIPR, the intracellular fluorescent dye is activated with light of a wavelength of 488 nm, which is generated by an argon laser, and the measuring parameters (laser power, illumination time and diaphragm of the CDD camera integrated into the FLIPR) are chosen such that the average value of the f fluorescent signal per well is between 30,000 and 35,000 relative fluorescence units.

The actual measurement in the FLIPR starts with a photograph being taken by the CCD camera every two seconds under software control. After 10 seconds, the increase in the intracellular pH is initiated by adding 90 µL of regeneration buffer (133.8 mM of NaCl, 4.7 mM of KCl, 1.25 mM of $MgCl_2$, 1.25 mM of $CaCl_2$, 0.97 mM of $K_2HPO_4$, 0.23 mM of $KH_2PO_4$, 10 mM of HEPES and 5 mM of glucose; pH 7.4 (adjusted with NaOH)) using a 96-well pipette device incorporated into the FLIPR.

Some wells, to which is added pure regeneration buffer, serve as positive controls (100% NHE activity). The negative controls (0% NHE activity) contain washing buffer. Regeneration buffer with twice the concentration of test substance is added to all the other wells. Measurement in the FLIPR terminates after 60 measurements (two minutes).

The experimental data allow the NHE activities to be calculated for each concentration of test substance and, from these, the $IC_{50}$ values of the substances. For the NHE-1 subtype the following results are obtained.

| example No. | $IC_{50}$ (NHE1)/nM |
| --- | --- |
| 1 | 49 |
| 2 | 22 |
| 3 | 67 |
| 4 | 96 |
| 5 | 51 |
| 6 | 44 |
| 7 | 90 |
| 8 | 121 |
| 9 | 0.25 |
| 10 | 0.16 |
| 11 | 19 |
| 12 | 0.5 |
| 13 | 0.1 |
| 14 | 2.3 |
| 15 | 2.6 |
| 16 | 3.1 |
| 17 | 10.7 |
| 18 | 1.6 |
| 19 | 42.9 |
| 20 | 0.8 |
| 21 | 29 |
| 22 | 0.2 |
| 23 | 97.7 |
| 24 | 222 |
| 25 | 29 |
| 26 | 3.6 |
| 27 | 0.6 |
| 28 | 192 |
| 29 | 4.3 |
| 30 | 17 |

The invention relates also to the use of the compound of formula I and/or its pharmaceutically acceptable salt thereof for the preparation of a medicament and a pharmaceutical composition as inhibitors of the NHE. Claimed is a medicine for human, veterinary or phytoprotective use, comprising a pharmaceutically effective amount of a compound of formula I and/or a pharmaceutically acceptable salt thereof, together with pharmaceutically acceptable carriers and additives, alone or in combination with other active pharmaceutical ingredients or medicaments.

The pharmaceutical composition according to the invention consists of a compound of formula I and/or a pharmaceutically acceptable salt thereof, in pure form or in the form of a composition in which it is combined with any other pharmaceutically compatible product, which may be inert or physiologically active. The medicament according to the invention can be administered, for example, orally, parenterally, intravenously, rectally, transdermally, topically or by inhalation. The medicament generally comprises an active ingredient of formula I and/or its pharmaceutically acceptable salt therof in an amount of from 0.001 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavourings, preservatives, solubilizers or colors.

For a pharmaceutical formulation for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers that can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

Tablets, pills, powders (gelatine capsules or cachets) or granules can be used as solid compositions for oral administration. In these compositions, the active principle according to the invention is mixed with one or more inert diluents, such as starch, cellulose, sucrose, lactose or silica, under a stream of argon. These compositions may also comprise substances other than diluents, for example one or more lubricants, such as magnesium stearate or talc, a colorant, a coating (dragees) or a varnish.

Pharmaceutically acceptable solutions, suspensions, emulsions, syrups and elixirs comprising inert diluents, such as water, ethanol, glycerol, plant oils or liquid paraffin, can be used as liquid compositions for oral administration. These compositions may comprise substances other than diluents, for example wetting products, sweeteners, thickeners, flavourings or stabilisers.

The sterile compositions for parenteral administration may preferably be aqueous or non-aqueous solutions, suspensions or emulsions. Solvents or vehicles that can be used include water, propylene glycol, a polyethylene glycol, plant oils, in particular olive oil, injectable organic esters, for example ethyl oleate, or other suitable organic solvents. These compositions may also comprise adjuvants, in particular wetting agents, tonicity agents, emulsifiers, dispersants and stabilisers. The sterilisation may be performed in several ways, for example by aseptic filtration, by incorporating sterilising agents into the composition, by irradiation or by heating. They may also be prepared in the form of sterile solid compositions that may be dissolved at the time of use in sterile water or any other injectable sterile medium.

The compositions for rectal administration are suppositories or rectal capsules that comprise, besides the active product, excipients, such as cocoa butter, semi-synthetic glycerides or polyethylene glycols.

The compositions for topical administration may be, for example, creams, lotions, eye drops, mouthwashes, nasal drops or aerosols.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of formula I and/or the pharmaceutically acceptable salts thereof in a pharmaceutically acceptable solvent such as, in particular, ethanol or water, or a mixture of such solvents. Formulation may, if required, also contain other pharmaceutical excipients such as surfactants, emulsifiers and stabilizers, and a propellant gas. Such a preparation contains, for example, the active ingredient in a concentration of about 0.1 to 10, in particular of about 0.3 to 3% by weight.

The dosage of the active ingredient of formula I to be administered, and the frequency of administration, depend on the desired effect, the potency and duration of action of the compounds used; additionally also on the nature and severity of the disorder to be treated and on the sex, age, weight and individual responsiveness of the mammal to be treated. In general, the doctor will determine the appropriate dosage as a function of the age and weight and all the other factors specific to the individual to be treated.

On average, the daily dose of a compound of formula I and/or the pharmaceutically acceptable salts thereof for a patient weighing about 75 kg is at least 0.001 mg/kg, preferably 1 mg/kg, to a maximum of 1000 mg/kg, preferably 100 mg/kg, of body weight. For acute episodes of the disorder, for example immediately after suffering a myocardial infarction, higher and, in particular, more frequent dosages may also be necessary, e.g. up to 4 single doses a day. Up to 2000 mg a day may be necessary, in particular on i.v. administration, for example for a patient with infarction in the intensive care unit, and the compounds of the invention can be administered by infusion.

The following examples illustrate compositions according to the invention:

Example A

Gel capsules containing a 50 mg dose of active product, having the composition below, can be prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

Example B

Tablets comprising a 50 mg dose of active product, having the composition below, can be prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethyl starch | 22 mg |

-continued

| | |
|---|---|
| Talc | 10 mg |
| Magnesium stearate | 2 mg |
| Colloidal silica | 2 mg |
| Mixture of hydroxymethylcellulose, glycerol and titanium oxide (72/3.5/24.5) qs 1 finished film-coated tablet weighing 245 mg | |

Example C

An injectable solution comprising 10 mg of active product, having the composition below, can be prepared:

| | |
|---|---|
| Compound of formula (I) | 10 mg |
| Benzoic acid | 80 mg |
| Benzyl alcohol | 0.06 mL |
| Sodium benzoate | 80 mg |
| 95% ethanol | 0.4 mL |
| Sodium hydroxide | 24 mg |
| Propylene glycol | 1.6 mL |
| Water | qs 4 mL |

We claim:
1. A compound of formula (I)

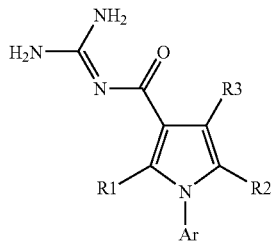

wherein
$R_1$ is hydrogen or methyl,
$R_2$ is hydrogen or $C_1$–$C_6$ alkyl,
$R_3$ is hydrogen, $C_1$–$C_6$ alkyl, $C_3$–$C_6$ cycloalkyl, halogen, $C_1$–$C_6$ hydroxyalkyl, $C_1$–$C_6$ alkyl-$NR_aR_b$, $NR_aR_b$, $S(O)_n$ $R_4$ or $C_1$–$C_6$ polyfluoroalkyl,
n is 0, 1 or 2,
Ar is a 6-membered monocyclic or a 10-membered bicyclic heteroaryl having one or two nitrogen atoms, which may be linked via any of its positions and which is optionally substituted on all their other positions with $C_1$–$C_6$ alkyl, halogen, nitro, $NR_aR_b$, $C_1$–$C_4$ alkylcarbonylamino, hydroxy, $C_1$–$C_6$ alkoxy, $S(O)_nR_4$, $CO_2H$, $C_1$–$C_6$ alkoxycarbonyl, $C_1$–$C_6$ alkylcarbonyl, $CONR_aR_b$, CN, $C_1$–$C_4$ polyfluoroalkyl, $C_1$–$C_3$ polyfluoroalkoxy or $SO_3H$,
$R_a$ and $R_b$ are each, independently, hydrogen, linear or branched $C_1$–$C_6$ alkyl, or $R_a$ and $R_b$ form, together with the nitrogen atom to which they are attached, a 5- or 6-membered heterocycle, which optionally contain another heteroatom chosen from O, S and N,
and
$R_4$ is $C_1$–$C_6$ alkyl, $C_1$–$C_6$ alkylamino or $NH_2$, or a racemic mixture, enantiomer, diastereomer, or tautomer of such compound, or a mixture thereof, or a pharmaceutically acceptable salt of such compound, racemic mixture, enantiomer, diastereomer, tautomer, or mixture.

2. A compound according to claim 1, wherein
$R_1$ is hydrogen or methyl,
$R_2$ is hydrogen or $C_1$–$C_6$ alkyl,
$R_3$ is hydrogen, $C_1$–$C_6$ alkyl, $C_3$–$C_6$ cycloalkyl, halogen, $C_1$–$C_6$ hydroxyalkyl, $C_1$–$C_6$ alkyl-$NR_aR_b$, $NR_aR_b$, $S(O)_n$ $R_4$ or $C_1$–$C_6$ polyfluoroalkyl,
n is 0, 1 or 2,
Ar is quinoline, isoquinoline, pyridine, pyrimidine or cinnoline, which may be linked via any of its positions and which is optionally substituted on all their other positions with $C_1$–$C_6$ alkyl, halogen, nitro, $NR_aR_b$, $C_1$–$C_4$ alkylcarbonylamino, hydroxy, $C_1$–$C_6$ alkoxy, $S(O)_nR_4$, $CO_2H$, $C_1$–$C_6$ alkoxycarbonyl, $C_1$–$C_6$ alkylcarbonyl, $CONR_aR_b$, CN, $C_1$–$C_4$ polyfluoroalkyl, $C_1$–$C_3$ polyfluoroalkoxy or $SO_3$ H,
$R_a$ and $R_b$ are each, independently, hydrogen, linear or branched $C_1$–$C_6$ alkyl having or $R_a$ and $R_b$ form, together with the nitrogen atom to which they are attached, a 5- or 6-membered heterocycle, which optionally contain another hetero atom chosen from O, S and N,
and
$R_4$ is $C_1$–$C_6$ alkyl, $C_1$–$C_6$ alkylamino or $NH_2$.

3. A compound according to claim 1, wherein
$R_1$ is hydrogen or methyl,
$R_2$ is hydrogen or $C_1$–$C_6$ alkyl,
$R_3$ is hydrogen, methyl, cyclopropyl or $CF_3$,
Ar is quinoline, isoquinoline, pyridine, pyrimidine or cinnoline, which may be linked via any of its positions and which is optionally substituted on all their other positions with $C_1$–$C_6$ alkyl, halogen, nitro, $NR_aR_b$, $C_1$–$C_4$ alkylcarbonylamino, hydroxy, $C_1$–$C_6$ alkoxy, $S(O)_nR_4$, $CO_2H$, $C_1$–$C_6$ alkoxycarbonyl, $C_1$–$C_6$ alkylcarbonyl, $CONR_aR_b$, CN, $C_1$–$C_4$ polyfluoroalkyl, $C_1$–$C_3$ polyfluoroalkoxy or $SO_3$ H,
n is 0, 1 or 2,
$R_a$ and $R_b$ Are each, independently, hydrogen, linear or branched $C_1$–$C_6$ alkyl or $R_a$ and $R_b$ form, together with the nitrogen atom to which they are attached, a 5- or 6-membered heterocycle, which optionally contain another hetero atom chosen from O, S and N,
and
$R_4$ is $C_1$–$C_6$ alkyl, $C_1$–$C_6$ alkylamino or $NH_2$.

4. A compound according to claim 1, which is:
3-guanidinocarbonyl-1-(quinol-2-yl)-1H-pyrrole,
3-guanidinocarbonyl-1-(quinol-4-yl)-1H-pyrrole,
3-guanidinocarbonyl-2-methyl-1-(quinol-4-yl)-1H-pyrrole,
3-guanidinocarbonyl-2-methyl-1-(quinol-2-yl)-1H-pyrrole,
3-guanidinocarbonyl-1-(isoquinol-1-yl)-1H-pyrrole,
3-guanidinocarbonyl-1-(isoquinol 1-yl)-2-methyl-1H-pyrrole,
3-guanidinocarbonyl-1-(quinol-5-yl)-1H-pyrrole,
3-guanidinocarbonyl-1-(quinol-8-yl)-1H-pyrrole,
3-guanidinocarbonyl-1-(isoquinol-4-yl)-1H-pyrrole,
3-guanidinocarbonyl-4-methyl-1-(quinol-4-yl)-1H-pyrrole,
3-guanidinocarbonyl-1-(isoquinol-1-yl)-4-methyl-1H-pyrrole,
3-guanidinocarbonyl-4,5-dimethyl-1-(quinol-4-yl)-1H-pyrrole,
3-guanidinocarbonyl-4-methyl-1-(quinol-5-yl)-1H-pyrrole, 3-guanidinocarbonyl-4-methyl-1-(quinol-2-yl)-1H-pyrrole,
3-guanidinocarbonyl-4-cyclopropyl-1-(quinol-4-yl)-1H-pyrrole,
3-guanidinocarbonyl-4-isopropyl-1-(quinol-4-yl)-1H-pyrrole,
3-guanidinocarbonyl-4-trifluoromethyl-1-(quinol-4-yl)-1H-pyrrole,
3-guanidinocarbonyl-4-dimethylamino-1-(quinol-4-yl)-1H-pyrrole,
3-guanidinocarbonyl-4-chloro-1-(quinol-4-yl)-1H-pyrrole,
3-guanidinocarbonyl-1-(2-methylquinol-4-yl)-1H-pyrrole,
3-guanidinocarbonyl-4-methyl-1-(2-methylquinol-4-yl)-1H-pyrrole,
3-guanidinocarbonyl-1-(6-chloroquinol-4-yl)-1H-pyrrole,
3-guanidinocarbonyl-4-methyl-1-(6-chloroquinol-4-yl)-1H-pyrrole,
3-guanidinocarbonyl-1-(7-chloroquinol-4-yl)-1H-pyrrole,
3-guanidinocarbonyl-4-methyl-1-(7-chloroquinol-4-yl y 1H-pyrrole,
3-guanidinocarbonyl-1-(8-chloroquinol-4-yl)-1H-pyrrole,
3-guanidinocarbonyl-4-methyl-1-(8-chloroquinol-4-yl)-1H-pyrrole,
3-guanidinocarbonyl-1-(7-chloro-2-methylquinol-4-yl)-1H-pyrrole,
3-guanidinocarbonyl-4-methyl-1-(7-chloro-2-methylquinol-4-yl)-1H-pyrrole,
3-guanidinocarbonyl-1-(6-fluoroquinol-4-yl)-1H-pyrrole,
3-guanidinocarbonyl-4-methyl-1-(6-fluoroquinol-4-yl)-1H-pyrrole,
3-guanidinocarbonyl-1-(8-fluoroquinol-4-yl)-1H-pyrrole,
3-guanidinocarbonyl-4-methyl-1-(8-fluoroquinol-4-yl)-1H-pyrrole,
3-guanidinocarbonyl-1-(6-fluoro-2-methylquinol-4-yl)-1H-pyrrole,
3-guanidinocarbonyl-4-methyl-1-(6-fluoro-2-methylquinol-4-yl)-1H-pyrrole,
3-guanidinocarbonyl-1-(7-fluoro-2-methylquinol-4-yl)-1H-pyrrole,
3-guanidinocarbonyl-4-methyl-1-(7-fluoro-2-methylquinol-4-yl)-1H-pyrrole,
3-guanidinocarbonyl-1-(8-fluoro-2-methylquinol-4-yl)-1H-pyrrole,
3-guanidinocarbonyl-4-methyl-1-(8-fluoro-2-methylquinol-4-yl)-1H-pyrrole,
3-guanidinocarbonyl-1-(6,8-difluoroquinol-4-yl)-1H-pyrrole,
3-guanidinocarbonyl-4-methyl-1-(6,8-difluoroquinol-4-yl)-1H-pyrrole,
3-guanidinocarbonyl-4-methyl-1-(6-methoxyquinol-4-yl)-1H-pyrrole,
3-guanidinocarbonyl-4-methyl-1-(6-hydroxyquinol-4-yl)-1H-pyrrole,
3-guanidinocarbonyl-4-methyl-1-(7-methoxyquinol-4-yl)-1H-pyrrole,
3-guanidinocarbonyl-4-methyl-1-(7-hydroxyquinol-4-yl)-1H-pyrrole,
3-guanidinocarbonyl-4-methyl-1-(6-trifluoromethylquinol-4-yl)-1H-pyrrole,
3-guanidinocarbonyl-4-methyl-1-(7-trifluoromethylquinol-4-yl)-1H-pyrrole,
3-guanidinocarbonyl-1-(isoquinol-1-yl)-4-trifluormethyl-1H-pyrrole,
3-guanidinocarbonyl-1-(1-cinnolin-4-yl)-1H-pyrrole,
3-guanidinocarbonyl-4-methyl-1-(pyrimidin-2-yl)-1H-pyrrole,
3-guanidinocarbonyl-4-methyl-1-(pyridin-2-yl)-1H-pyrrole,
3-guanidinocarbonyl-4-methyl-1-(pyridin-3-yl)-1H-pyrrole,
3-guanidinocarbonyl-4-methyl-1-(pyrimidin-5-yl)-1H-pyrrole, or
3-guanidinocarbonyl-4-methyl-1-(quinolin-3-yl)-1H-pyrrole, or a tautomer thereof or a pharmaceutically acceptable salt of such compound or tautomer.

5. A pharmaceutical composition for human, veterinary, or phytoprotective use comprising a pharmaceutically effective amount of a compound according to claim 1 and a pharmaceutically acceptable medium.

6. A pharmaceutical composition for human, veterinary, or phytoprotective use comprising a pharmaceutically effective amount of a compound according to claim 1 together with a pharmaceutically acceptable medium in combination with a pharmaceutically effective amount of other pharmacologically active ingredients or medicaments.

7. A method of treatment, by inhibiting the cellular sodium-proton antiporter (Na+/H+ exchanger) activity of a patient in need thereof, for the treatment of cardiovascular diseases, metabolic diseases, cancerous diseases or fibrotic diseases, in a patient in need thereof, comprising administering to the patient a pharmaceutically effective amount of a compound according to claim 1.

8. A method for the treatment, by inhibiting the cellular sodium-proton antiporter (Na+/H+ exchanger) activity of a patient in need thereof, for the treatment of acute or chronic damage to, or disorders or indirect sequelae of organs and tissues caused by ischemic or reperfusion events;

arrhythmias, life-threatening cardiac ventricular fibrillation, myocardial infarction, angina pectoris;

ischemic states of the heart, ischemic states of the peripheral and central nervous system, stroke, cerebral oedema attack, ischemic states of peripheral organs and tissues;

state of stroke;

diseases in which cellular proliferation represents s primary or secondary cause;

cancer, metastasis, prostate hypertrophy, prostate hyperplasia;

atherosclerosis, disturbances of lipid metabolism, high blood pressure;

disorders of the central nervous system;

non-insulin-dependent diabetes mellitus (NIDDM), late damage from diabetes;

thromboses, disorders resulting from endothelial dysfunction, intermittent claudication;

fibrotic disorders of internal organs, fibrotic disorders of the liver, fibrotic disorders of the kidney, fibrotic disorders of vessels, fibrotic disorders of lung, fibrotic disorders of the heart;

heart failure, congestive heart failure, acute or chronic inflammatory disorders, disorders caused by protozoa;

malaria, or coccidiosis in poultry, comprising administering to a patient in need thereof, a pharmaceutically effective amount of a compound according to claim 1.

9. A method according to claim 8 for the treatment of allergic shock, cardiogenic shock, hypovolaemic shock or bacterial shock.

10. A method according to claim 8 for the treatment of essential hypertension.

11. A method according to claim 8 for the treatment of disorders resulting from overexcitability of the CNS.

12. A method according to claim 11, for the treatment of epilepsy or centrally induced convulsions.

13. A method according to claim 8 for the treatment of anxiety states, depressions or psychoses.

14. A method, by inhibiting the cellular sodium-proton antiporter (Na+/H+ exchanger) activity of a patient in need thereof, for protecting an organ in a transplant donor during organ transplantation, both before and during the removal of the organ, comprising administering to said donor, a pharmaceutically effective amount of a compound according to claim 1.

15. A method, by inhibiting the cellular sodium-proton antiporter (Na+/H+ exchanger) activity of a patient in need thereof, for protecting a removed organ during treatment with, or storage in physiological bath liquids, comprising contacting said organ with a pharmaceutically effective amount of a compound according to claim 1.

16. A method, by inhibiting the cellular sodium-proton antiporter (Na+/H+ exchanger) activity of a patient in need thereof, for protecting a removed organ during transfer to a recipient organism during organ transplantation, comprising contacting said organ with a pharmaceutically effective amount of a compound according to claim 1.

17. A method, by inhibiting the cellular sodium-proton antiporter (Na+/H+ exchanger) activity of a patient in need thereof, for the treatment or reduction of the cardiotoxic effects in thyrotoxicosis in a patient in need thereof, comprising administering to said patient a pharmaceutically effective amount of a compound according to claim 1.

18. A method of treatment, by inhibiting the cellular sodium-proton antiporter (Na+/H+ exchanger) activity of a patient in need thereof, for the treatment of acute or chronic damage, disorders or indirect sequelae of organs or tissues caused by ischemic or reperfusion events in a patient in need thereof, comprising administering to said patient a pharmaceutically effective amount of a compound according to claim 1.

19. A method, by inhibiting the cellular sodium-proton antiporter (Na+/H+ exchanger) activity of a patient in need thereof, for the treatment of life-threatening cardiac ventricular fibrillation, in a patient in need thereof, comprising administering to said patient, a pharmaceutically effective amount of a compound according to claim 1.

20. A method, by inhibiting the cellular sodium-proton antiporter (Na+/H+ exchanger) activity of a patient in need thereof, for the treatment or prophylaxis of metastasis in a patient in need thereof, comprising administering to said patient a pharmaceutically effective amount of a compound according to claim 1.

21. A method, by inhibiting the cellular sodium-proton antiporter (Na+/H+ exchanger) activity of a patient in need thereof, for the treatment of fibrotic disorders of the heart, heart failure, or congestive heart failure, in a patient in need thereof, comprising administering to said patient a pharmaceutically effective amount of a compound according to claim 1.

22. A method, by inhibiting the cellular sodium-proton antiporter (Na+/H+ exchanger) activity of a patient in need thereof, for the treatment of a disease which is related to NHE, in a patient in need thereof, comprising administering to said patient a pharmaceutically effective amount of a compound according to claim 1.

23. A method, by inhibiting the cellular sodium-proton antiporter (Na+/H+ exchanger) activity of a patient in need thereof, for protecting the organs or blood vessels during surgical intervention, in a patient in need thereof, comprising administering to such patient a pharmaceutically effective amount of a compound according to claim 1.

24. A process for preparing a compound according to claim 1 characterised in that

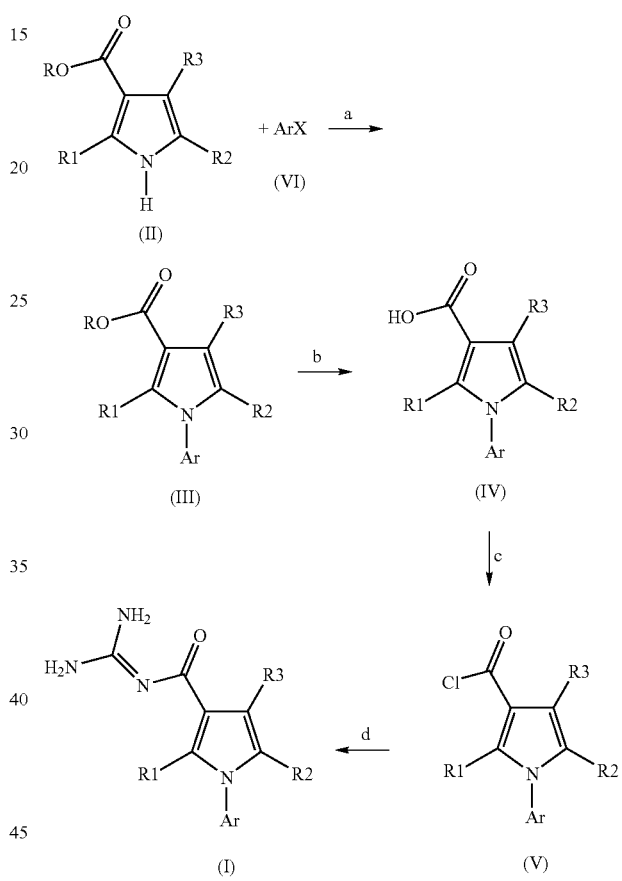

a) a heteroaryl halide ArX of formula (VI) is reacted with a 3-alkoxycarbonyl-1H-pyrrole of formula (II)

b) the obtained 3-alkoxycarbonyl-1-heteroaryl-1H-pyrrole of formula (III) is saponified c) the 3-carboxy-1-heteroaryl-1H-pyrrole of formula(IV) is converted in the acid chloride of formula (V)

d) the obtained product of formula (V) is reacted with guanidine, the product is isolated and is optionally converted into a pharmaceutically acceptable salt, wherein in the compounds of formula II, III, IV, V, and VI Ar and $R_1$ to $R_3$ are defined as in claim 1 to 4, X is F, Cl, Br or I and, R is $C_1$–$C_6$ alkyl.

25. A process for preparing a compound according to claim 1 characterised in that

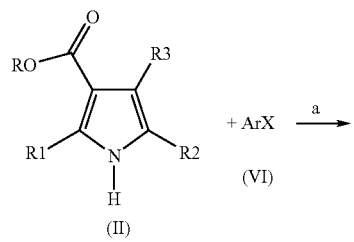

(II)

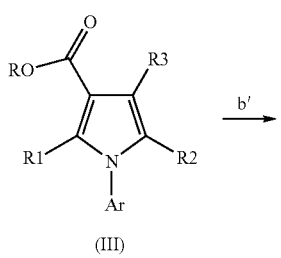

(III)

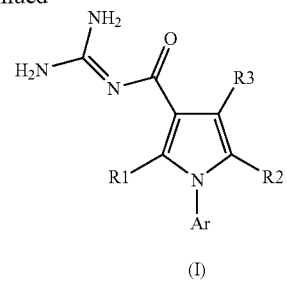

(I)

a) a heteroaryl halide ArX of formula (VI) is reacted with a 3-alkoxycarbonyl-1H-pyrrole of formula (II)
b') the obtained 3-alkoxycarbonyl-1-heteroaryl-1H-pyrrole (III) is reacted with guanidine, the product is isolated and is optionally converted into a pharmaceutically acceptable salt, wherein in the compounds of formula II, III and VI
Ar and $R_1$ to $R_3$ are defined as in claim 1 to 4,
X is F, Cl, Br or I and,
R is $C_1$–$C_6$ alkyl.

* * * * *